US009439013B2

(12) United States Patent
Adachi et al.

(10) Patent No.: US 9,439,013 B2
(45) Date of Patent: Sep. 6, 2016

(54) UNCOMFORTABLE SOUND PRESSURE EVALUATION SYSTEM, UNCOMFORTABLE SOUND PRESSURE EVALUATION APPARATUS, UNCOMFORTABLE SOUND PRESSURE ADJUSTMENT APPARATUS, UNCOMFORTABLE SOUND PRESSURE EVALUATION METHOD, AND COMPUTER PROGRAM THEREOF

(71) Applicant: Panasonic Corporation, Osaka (JP)

(72) Inventors: Shinobu Adachi, Nara (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 197 days.

(21) Appl. No.: 14/500,163

(22) Filed: Sep. 29, 2014

(65) Prior Publication Data

US 2015/0016618 A1 Jan. 15, 2015

Related U.S. Application Data

(63) Continuation of application No. PCT/JP2013/005263, filed on Sep. 5, 2013.

(30) Foreign Application Priority Data

Sep. 27, 2012 (JP) .................................. 2012-214015

(51) Int. Cl.
*H04R 29/00* (2006.01)
*A61B 5/0484* (2006.01)
(Continued)

(52) U.S. Cl.
CPC ............. *H04R 29/00* (2013.01); *A61B 5/0484* (2013.01); *A61B 5/125* (2013.01); *A61B 5/726* (2013.01); *H04R 25/70* (2013.01)

(58) Field of Classification Search
CPC ...... H04R 25/70; H04R 2/90; H04R 25/502; A61B 5/121
USPC ............ 381/56, 60, 312, 514, 321; 600/559, 600/585; 73/647, 585
See application file for complete search history.

(56) References Cited

U.S. PATENT DOCUMENTS 4,276,781 A * 7/1981 Leitner .................. A61B 5/121
  73/647
9,044,157 B2 * 6/2015 Adachi ............. A61B 5/04845
(Continued)

FOREIGN PATENT DOCUMENTS

JP 2004-179965 A 6/2004
JP 3106663 U 11/2004
(Continued)

OTHER PUBLICATIONS

International Search Report for corresponding International Application No. PCT/JP2013/005263 dated Oct. 8, 2013.
(Continued)

*Primary Examiner* — Melur Ramakrishnaiah
(74) *Attorney, Agent, or Firm* — Renner, Otto, Boisselle & Sklar, LLP

(57) ABSTRACT

An exemplary uncomfortable sound pressure evaluation system consecutively presents sound stimulation groups to a user. Each sound stimulation group includes a sound stimulation, and the sound stimulation groups differ in frequency from one another. The system includes: an extraction section configured to extract, for each sound stimulation group, information concerning event-related potential relating to the sound stimulation; an estimation section configured to estimate an uncomfortable sound pressure (UCL) of the user from the information concerning event-related potential; and a correction section configured to determine whether the estimated UCL is higher than a predefined maximum UCL or not, and if a proportion of those determination results which indicate the UCL to be higher than the maximum UCL is smaller than predetermined, correcting each UCL determined as higher than the maximum UCL to a sound pressure equal to or less than the maximum UCL.

20 Claims, 16 Drawing Sheets

(51) Int. Cl.
*A61B 5/00* (2006.01)
*A61B 5/12* (2006.01)
*H04R 25/00* (2006.01)

(56) References Cited

U.S. PATENT DOCUMENTS

| | | |
|---|---|---|
| 2001/0049480 A1 | 12/2001 | John et al. |
| 2004/0064066 A1 | 4/2004 | John et al. |
| 2004/0204659 A1 | 10/2004 | John et al. |
| 2013/0138012 A1 | 5/2013 | Morikawa et al. |

FOREIGN PATENT DOCUMENTS

| | | |
|---|---|---|
| JP | 2009-288354 A | 12/2009 |
| WO | WO 01/87147 A1 | 11/2001 |
| WO | WO 2008/038650 A1 | 4/2008 |

OTHER PUBLICATIONS

Shinobu Adachi et al., "Estimating uncomfortable loudness levels based on event-related potentials to triplets of auditory stimuli", Proceedings of the 51th Japanese Society for Medical and Biological Engineering, O1-10-1, 2012.

Jishoukanrendeni (ERP) Manyuaru—P300 Wo Chushinni—(or "Event-Related Potential (ERP) Manual—mainly concerning P300-"), edited by Kimitaka Kaga et al., Shinohara Shuppan Shinsha, 1995, p. 30 and concise explanation.

D.P. Pascoe, "Clinical measurements of the auditory dynamic range and their relation to formulas for hearing aid gain", In lensen. H. I. (Ed.) Hearing Aid Fitting: Theoretical and Practical Views 13th Danavox Symposium. Copenhagen: Stougaard (1988).

J. N. Keller, "Loudness discomfort levels: A retrospective study comparing data from Pascoe (1988) and Washington University School of Medicine" (2006).

Takashi Kimitsuki, et al., "Inner ear auditory testing in patients with normal hearing showing hyperacusis", Audiology Japan 52, pp. 152-156, 2009 and concise explanation.

\* cited by examiner

*FIG.1*

| HTL (dB HL) | PREDICTED UCL (dB HL) |
|---|---|
| 0 | 97 |
| 5 | 99 |
| 10 | 99 |
| 15 | 98 |
| 20 | 97 |
| 25 | 101 |
| 30 | 102 |
| 35 | 101 |
| 40 | 103 |
| 45 | 105 |
| 50 | 107 |
| 55 | 108 |
| 60 | 110 |
| 65 | 114 |
| 70 | 115 |
| 75 | 117 |
| 80 | 120 |
| 85 | 120 |
| 90 | 124 |
| 95 | 130 |
| 100 | 127 |
| 105 | 133 |
| 110 | 134 |
| 115 | 137 |
| 120 | 140 |

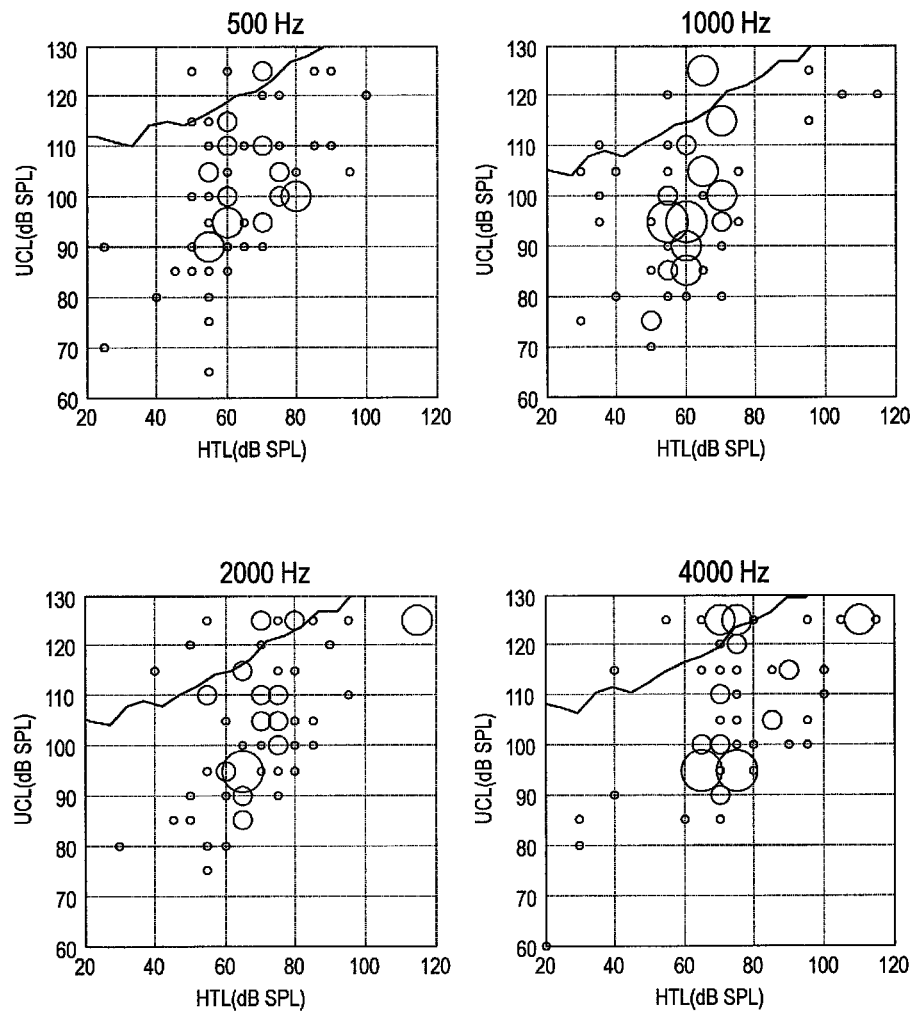

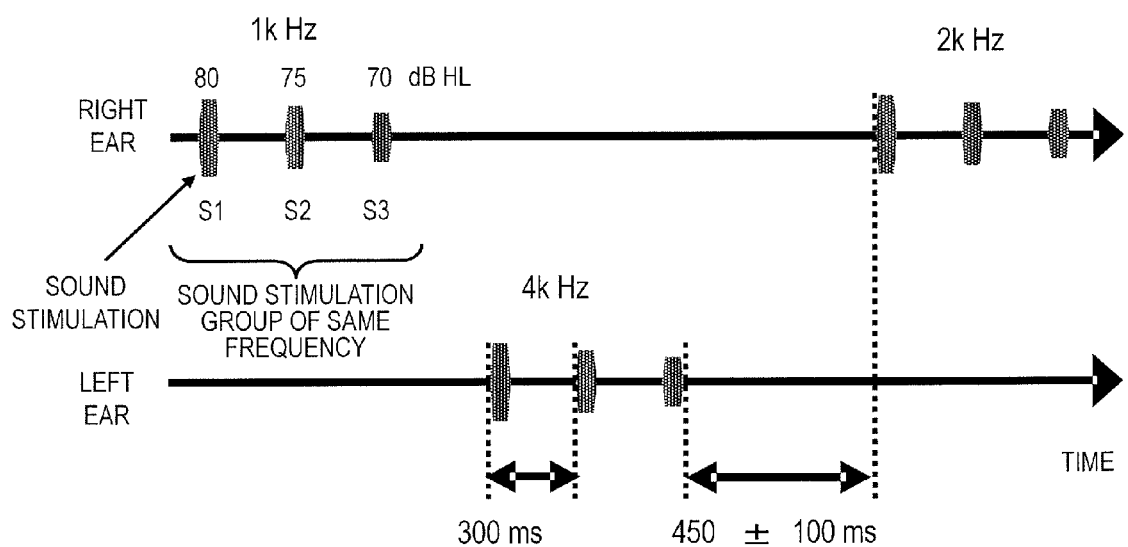

UPPER VIEW    FRONT VIEW

FIG.8

| HTL (dB HL) | PREDICTED UCL (dB HL) | | | |
|---|---|---|---|---|
| | 500 Hz | 1000 Hz | 2000 Hz | 4000 Hz |
| 0 | 100.7 | 104 | 97.7 | 98.6 |
| 5 | 95.9 | 99.6 | 96.7 | 97 |
| 10 | 100.4 | 100.6 | 100 | 99.2 |
| 15 | 98.2 | 99.9 | 94.6 | 97.9 |
| 20 | 99.1 | 97.9 | 96.9 | 98.5 |
| 25 | 98.9 | 94.7 | 99.1 | 97.4 |
| 30 | 97.2 | 98.8 | 94.3 | 7.3 |
| 35 | 95.9 | 98.1 | 94.5 | 6.3 |
| 40 | 98.2 | 96.9 | 97.6 | 97.8 |
| 45 | 98.7 | 95.9 | 96.4 | 97 |
| 50 | 98.3 | 101 | 98.3 | 99 |
| 55 | 102 | 98.9 | 99.5 | 100.5 |
| 60 | 99.4 | 99.5 | 103.3 | 101.2 |
| 65 | 100.9 | 105.4 | 106.8 | 104.8 |
| 70 | 105.1 | 107.2 | 107.4 | 107 |
| 75 | 106.6 | 108.7 | 106.4 | 107.7 |
| 80 | 117.3 | 107.1 | 117.3 | 112.2 |
| 85 | 103.3 | 109 | 112.8 | 110.4 |
| 90 | 105 | 110 | 104.5 | 110 |
| 95 | | 115 | 116.2 | 116.4 |
| 100 | | 105 | | 107.3 |
| 105 | | | | 110 |
| 110 | | | | |
| 115 | | | 115 | 115 |
| 120 | | | | |

(a) THREE USERS WITH PARTICULARLY LARGE UCL (b) 29 OTHER USERS

*FIG.13*

UNCOMFORTABLE SOUND PRESSURE (dBHL)

|  | 500 Hz | 1000 Hz | 2000 Hz | 4000 Hz |
|---|---|---|---|---|
| RIGHT | 110 | 105 | 100 | 100 |
| LEFT | 115 | 100 | 95 | 100 |

*FIG.16*

|  |  | RIGHT | | | | LEFT | | | |
|---|---|---|---|---|---|---|---|---|---|
|  |  | 500 Hz | 1k Hz | 2k Hz | 4k Hz | 500 Hz | 1k Hz | 2k Hz | 4k Hz |
| NUMBER OF SUMMA-TIONS | 1 | 90 | 100 | 85 | 70 | 70 | 70 | 70 | 75 |
| | 2 | 90 | 85 | 115 | 80 | 110 | 105 | 100 | 85 |
| | 3 | 85 | 110 | 90 | 110 | 115 | 95 | 70 | 110 |
| | 4 | 105 | 95 | 75 | 70 | 105 | 90 | 70 | 110 |
| | 5 | 100 | 85 | 115 | 115 | 70 | 115 | 95 | 70 |
| | 6 | 105 | 115 | 115 | 105 | 80 | 100 | 70 | 85 |
| | 7 | 115 | 110 | 90 | 90 | 85 | 100 | 110 | 95 |
| | 8 | 75 | 95 | 75 | 95 | 100 | 110 | 110 | 95 |
| | 9 | 115 | 100 | 80 | 95 | 75 | 110 | 105 | 95 |
| | 10 | 75 | 95 | 90 | 90 | 110 | 95 | 75 | |
| | 11 | 100 | 105 | 95 | 95 | 120 | 80 | 100 | |
| | 12 | 95 | 105 | 110 | 95 | 105 | 90 | 95 | |
| | 13 | 95 | 105 | 115 | | 100 | 95 | 100 | |
| | 14 | 100 | | 95 | | 105 | 100 | 100 | |
| | 15 | 100 | | 110 | | 105 | 95 | | |
| | 16 | 100 | | 120 | | 100 | 95 | | |
| | 17 | | | 115 | | 105 | | | |
| | 18 | | | 115 | | | | | |
| | 19 | | | 90 | | | | | |
| | 20 | | | 110 | | | | | |
| | ... | | | ... | | | | | |

*FIG.17*

|  | RIGHT | | | | LEFT | | | |
|---|---|---|---|---|---|---|---|---|
|  | 500 Hz | 1k Hz | 2k Hz | 4k Hz | 500 Hz | 1k Hz | 2k Hz | 4k Hz |
| CONVERGENCE DETERMINATION FOR ESTIMATION RESULT | 1 | 1 | 0 | 1 | 1 | 1 | 1 | 1 |

UNCOMFORTABLE SOUND PRESSURE EVALUATION SYSTEM, UNCOMFORTABLE SOUND PRESSURE EVALUATION APPARATUS, UNCOMFORTABLE SOUND PRESSURE ADJUSTMENT APPARATUS, UNCOMFORTABLE SOUND PRESSURE EVALUATION METHOD, AND COMPUTER PROGRAM THEREOF

This is a continuation of International Application No. PCT/JP2013/005263, with an international filing date of Sep. 5, 2013, which claims priority of Japanese Patent Application No. 2012-214015, filed on Sep. 27, 2012, the contents of which are hereby incorporated by reference.

BACKGROUND

1. Technical Field

The present disclosure relates to a technique of evaluating whether a speech sound has been heard in comfort. More specifically, the present disclosure relates to a technique of estimating an uncomfortable sound pressure with respect to a pure tone, in the context of "fitting" of a hearing aid or the like, i.e., adjusting an amount of amplification for each frequency of an external sound to arrive at a sound of a loudness which is appropriate to each individual user.

2. Description of the Related Art

In recent years, people who are suffering from hypacusia because of old age that need hearing aids are increasing in number. Their number is said to be about 20 million domestically, and about 500 million globally (as investigated by the Japan Hearing Instruments Manufacturers Association). Before beginning use of a hearing aid, "fitting" is required for adjusting the amount of sound amplification for each frequency in accordance with the auditory characteristics of the user.

For the sake of fitting, the user needs to visit a hearing aid shop several times to make readjustments because it is generally difficult to complete fitting in one time. One reason thereof is that an uncomfortable sound pressure (or uncomfortable loudness level: hereinafter referred to as "UCL") cannot be correctly measured. In a test based on subjective reporting where the subject himself or herself must hear an actually-generated sound to tell whether it presents an uncomfortable sound pressure or not, the need for such loud sounds impose psychological stress and fatigue on the subject; therefore, a UCL is often determined through calculation from a hearing threshold level. However, a problem of this is that a UCL which is universally calculated from a hearing threshold level will not reflect individual differences.

Accordingly, techniques for estimating UCL by using an electroencephalogram, which reflects electrical activities of the brain, are being developed in the recent years. "Estimating uncomfortable loudness levels based on event-related potentials to triplets of auditory stimuli", Shinobu ADACHI et al., Proceedings of the 51th Japanese Society for Medical and Biological Engineering, O1-10-1, 2012 (Hereinafter, Non-Patent Document 1) discloses a technique of estimating a UCL of a person with normal hearing with respect to each frequency, this technique using an electroencephalogram (auditory evoked potential) which is induced by triplet sounds of 80 dBHL or less, which is not loud. Since this technique utilizes an electroencephalogram of the subject when he or she hears a sound stimulation of a non-loud sound pressure for a short time, it is supposed to enable an individual UCL estimation.

SUMMARY

When a UCL is estimated by the aforementioned technique, there may be a relatively large error between an estimated UCL and an actually-measured UCL. Adjusting a hearing aid by using such an estimated UCL may possibly allow a sound which is overbearing to that user to be output from the hearing aid, thus making the user feel uncomfortable. The aforementioned conventional technique needs to be able to estimate UCL more accurately, such that overbearing sounds will hardly be output from the hearing aid.

One non-limiting, and exemplary embodiment of the present application presents an uncomfortable sound pressure evaluation system and the like which estimate UCL so that overbearing sounds will not be output from the hearing aid.

In order to solve the above problems, an uncomfortable sound pressure evaluation system according to one embodiment of the present invention comprises: a measurement section configured to measure an electroencephalogram signal of a user; an output configured to consecutively present a plurality of sound stimulation groups to the user, each sound stimulation group including at least one sound stimulation, and the sound stimulation groups differing in frequency from one another; an extraction section configured to extract, for each sound stimulation group, information concerning event-related potential from the electroencephalogram signal in a predetermined zone defined based on a point of presenting the at least one sound stimulation as a starting point; an estimation section configured to estimate an uncomfortable sound pressure of the user from the information concerning event-related potential against a predefined criterion; a storage section configured to store a predefined maximum uncomfortable sound pressure; and a correction section configured to determine whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

The general and specific embodiment above can be implemented as a system, a method, or a computer program, or implemented by using a combination of a system, a method, and/or a computer program.

With an uncomfortable sound pressure evaluation system according to an embodiment of the present invention, the maximum error of a UCL which is estimated as indexed by an electroencephalogram in response to a sound stimulation is reduced, and a safer hearing aid fitting is realized such that no overbearing sounds will be presented even when a hearing aid adjustment is made based on the result of estimation.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 1 is a diagram showing UCLs which are predicted based on HTL, as reported by Pascoe (1988).

FIG. 2 shows diagrams showing auditory characteristics distributions concerning HTLs and subjective UCLs of all participants with respect to different frequencies, pooled regardless of the right or left ear.

FIG. 3 is a diagram showing triplet sound stimulations in outline.

FIG. 8 is a diagram showing average UCLs for different HTLs, as reported by Keller (2006).

FIG. 13 is a diagram showing an example of data accumulation in a DB 80.

FIG. 16 is a diagram showing examples of estimated UCLs stored in a convergence determination section 68.

FIG. 17 is a diagram showing example results of convergence determination stored in the convergence determination section 68.

DETAILED DESCRIPTION

Figure 4A:
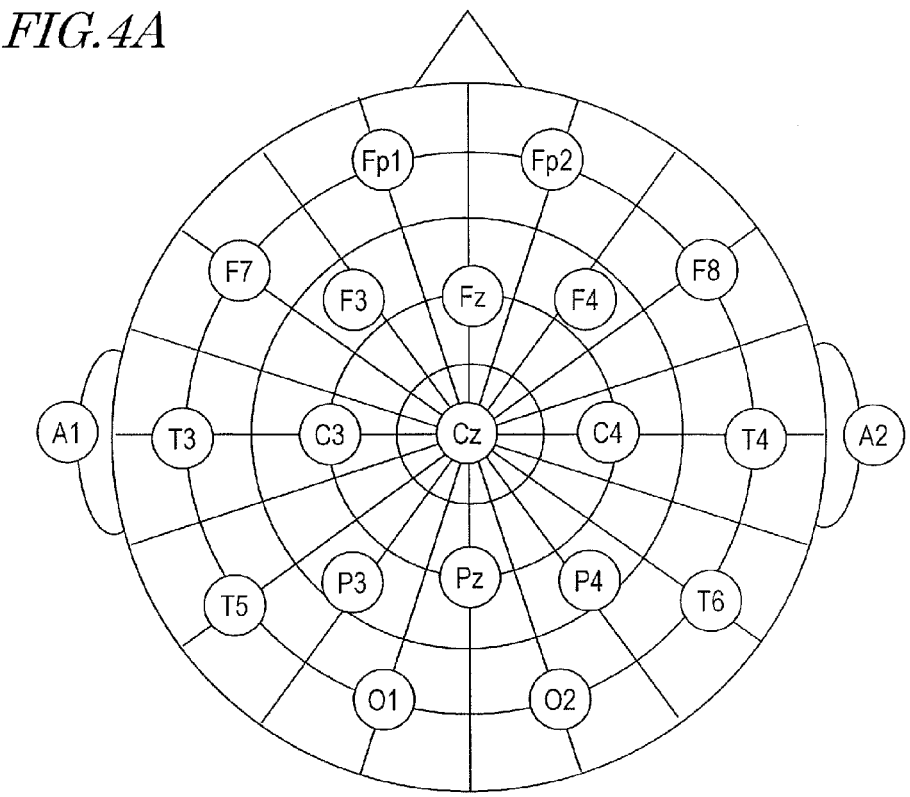
FIG. 4A is a diagram showing electrode positions according to the International 10-20 system (10-20 System).

In the technique disclosed in Non-Patent Document 1, the mean error between UCLs actually measured through subjective reporting and UCLs estimated from the electroencephalogram was 5 dB or less. However, a maximum error of 25 dB occurred at some frequency of some user. If the UCL is estimated to be 25 dB higher than the subjective UCL and a hearing aid adjustment is made by using this estimated UCL, there is a problem in that a sound which is overbearing to that user may be output from the hearing aid, thus making the user feel uncomfortable. When determining a UCL through estimation, there is a possibility of the aforementioned problem associated with estimation error.

The following is an outline of an embodiment(s) of the present invention.

An uncomfortable sound pressure evaluation system according to an embodiment of the present invention comprises: a measurement section configured to measure an electroencephalogram signal of a user; an output section configured to consecutively present a plurality of sound stimulation groups to the user, each sound stimulation group including at least one sound stimulation, and the sound stimulation groups differing in frequency from one another; an extraction section configured to extract, for each sound stimulation group, information concerning event-related potential from the electroencephalogram signal in a predetermined zone defined based on a point of presenting the at least one sound stimulation as a starting point; an estimation section configured to estimate an uncomfortable sound pressure of the user from the information concerning event-related potential against a predefined criterion; a storage section configured to store a predefined maximum uncomfortable sound pressure; and a correction section configured to determine whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

An uncomfortable sound pressure evaluation system according to another embodiment of the present invention comprises: a measurement section configured to measure an electroencephalogram signal of a user; an output section configured to present a sound stimulation group to the user, the sound stimulation group including a first sound, a second sound, and a third sound which are pure tones of a same frequency and which consecutively decrease in sound pressure within a predetermined range; an extraction section configured to extract a characteristic amount concerning time frequency information of event-related potential from the electroencephalogram signal in a predetermined zone defined based on a point of presenting each of the first sound, the second sound, and the third sound as a starting point; an estimation section configured to estimate, based on the extracted characteristic amount, an uncomfortable sound pressure corresponding to the frequency; a maximum uncomfortable sound pressure determination section configured to determine, based on a hearing threshold value of the user, a maximum uncomfortable sound pressure of the user corresponding to the frequency; and a correction section configured to correct the uncomfortable sound pressure to the maximum uncomfortable sound pressure and to output the corrected uncomfortable sound pressure if the estimated uncomfortable sound pressure is higher than the maximum uncomfortable sound pressure, and to output the estimated uncomfortable sound pressure if the estimated uncomfortable sound pressure is equal to or lower than the maximum uncomfortable sound pressure.

For example, the maximum uncomfortable sound pressure determination section retains in advance a predetermined table concerning maximum uncomfortable sound pressures associated with hearing threshold values, and determines the maximum uncomfortable sound pressure from a given hearing threshold value of the user by referring to the table.

For example, for each of a plurality of frequencies, the output section outputs a sound stimulation group including a first sound, a second sound, and a third sound; the extraction section extracts a characteristic amount concerning time frequency information of event-related potential for each sound stimulation group; the estimation section estimates an uncomfortable sound pressure corresponding to each frequency, based on the characteristic amount extracted for each sound stimulation group; and for the respective estimated uncomfortable sound pressure corresponding to each frequency, the correction section corrects the uncomfortable sound pressure to the maximum uncomfortable sound pressure and outputs the corrected uncomfortable sound pressure if the uncomfortable sound pressure is higher than the maximum uncomfortable sound pressure, and outputs the estimated uncomfortable sound pressure if the estimated uncomfortable sound pressure is equal to or lower than the maximum uncomfortable sound pressure.

For example, for each of a plurality of frequencies, the output section outputs a sound stimulation group including a first sound, a second sound, and a third sound; the extraction section extracts a characteristic amount concerning time frequency information of event-related potential for each sound stimulation group; the estimation section estimates an uncomfortable sound pressure corresponding to each frequency, based on the characteristic amount extracted for each sound stimulation group; and for the respective estimated uncomfortable sound pressure corresponding to each frequency, the correction section determines whether the uncomfortable sound pressure is higher than the maximum uncomfortable sound pressure or not, and if, among determination results, a proportion of those determination results which indicate the uncomfortable sound pressure to be higher than the maximum uncomfortable sound pressure is equal to or greater than predetermined, outputs the estimated uncomfortable sound pressure for all frequencies.

For example, among the determination results, if a proportion of those determination results which indicate the uncomfortable sound pressure to be higher than the maximum uncomfortable sound pressure is smaller than predetermined, the correction section corrects the uncomfortable sound pressure to the maximum uncomfortable sound pressure and outputs the corrected uncomfortable sound pressure, for each uncomfortable sound pressure determined to be higher than the maximum uncomfortable sound pressure.

For example, the uncomfortable sound pressure measurement system further comprises a database for accumulating the uncomfortable sound pressure that is output from the correction section for the frequency.

For example, the correction section generates correction information indicating whether the estimated uncomfortable sound pressure is corrected or not; and the database accumulates the correction information in association with the uncomfortable sound pressure for the frequency.

For example, the output section presents a sound stimulation group of the same frequency and sound pressures as those of the first sound, the second sound, and the third sound a plurality of times at a predetermined interval; each time the sound stimulation group is presented, the extraction section extracts an event-related potential from the electroencephalogram signal in a predetermined zone defined based on a point of presenting each of the first sound, the second sound, and the third sound of each sound stimulation group as a starting point, and adds the event-related potential to the already extracted event-related potential or event-related potentials; and each time the sound stimulation group is presented, the estimation section estimates an uncomfortable sound pressure based on the added event-related potential.

For example, the uncomfortable sound pressure evaluation system further comprises a convergence determination section configured to determine, each time the sound stimulation group is presented, whether the estimated uncomfortable sound pressure has converged or not, wherein, for any sound stimulation group being determined by the convergence determination section as having reached convergence, the output section stops subsequent presentation.

For example, the extraction section extracts a wavelet-coefficient related characteristic amount concerning the event-related potential.

For example, the estimation section retains as training data a previously-provided relationship between wavelet characteristic amounts and sound pressures of other people, and performs linear discrimination by using the characteristic amount extracted by the extraction section and the training data to estimate the uncomfortable sound pressure.

For example, based on an event-related potential of the electroencephalogram signal extraction section measured in a time zone of 300 ms or less defined from a point of presenting each of the first sound, the second sound, and the third sound as a starting point, and extracts a wavelet coefficient of the event-related potential as the characteristic amount.

For example, the extraction section extracts as the characteristic amount a value obtained by averaging wavelet coefficients of the event-related potential over a predetermined frequency range and a predetermined time range.

For example, the predetermined frequency range is between 5 Hz and 15 Hz.

For example, the predetermined time range is 50 ms.

An uncomfortable sound pressure adjustment apparatus according to still another embodiment of the present invention is an uncomfortable sound pressure adjustment apparatus for use in an uncomfortable sound pressure evaluation system, the uncomfortable sound pressure evaluation system including an output section configured to consecutively present a plurality of sound stimulation groups to a user, each sound stimulation group including at least one sound stimulation, and the sound stimulation groups differing in frequency from one another, the uncomfortable sound pressure adjustment apparatus comprising: an extraction section configured to receive from a measurement section which measures an electroencephalogram signal of the user the electroencephalogram signal, and for each sound stimulation group, extracting information concerning event-related potential from the electroencephalogram signal in a predetermined zone defined based on a point of presenting the at least one sound stimulation as a starting point; an estimation section configured to estimate an uncomfortable sound pressure of the user from the information concerning event-related potential against a predefined criterion; a storage section configured to store a predefined maximum uncomfortable sound pressure; and a correction section configured to determine whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

An uncomfortable sound pressure evaluation apparatus according to still another embodiment of the present invention comprises: the uncomfortable sound pressure adjustment apparatus of claim 17; a sound stimulation determination section configured to determine the at least one sound stimulation; and a sound stimulation generation section configured to generate the determined at least one sound stimulation, and to output to the extraction section information of a point of outputting the at least one sound stimulation.

An uncomfortable sound pressure evaluation method according to still another embodiment of the present invention comprises the steps of: receiving from a measurement section which measures an electroencephalogram signal of a user the electroencephalogram signal; consecutively presenting a plurality of sound stimulation groups to the user, each sound stimulation group including at least one sound stimulation, and the sound stimulation groups differing in frequency from one another; for each sound stimulation group, extracting information concerning event-related potential from the electroencephalogram signal in a predetermined zone defined based on a point of presenting the at least one sound stimulation as a starting point; estimating an uncomfortable sound pressure of the user from the information concerning event-related potential against a predefined criterion; and determining whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

A computer program according to still another embodiment of the present invention is a computer program to be executed by a computer mounted in an uncomfortable sound pressure evaluation apparatus, wherein the computer program causes the computer to execute the steps of: receiving from a measurement section which measures an electroencephalogram signal of a user the electroencephalogram signal; consecutively presenting a plurality of sound stimulation groups to the user, each sound stimulation group including at least one sound stimulation, and the sound stimulation groups differing in frequency from one another; for each sound stimulation group, extracting information concerning event-related potential from the electroencephalogram signal in a predetermined zone defined based on a point of presenting the at least one sound stimulation as a starting point; estimating an uncomfortable sound pressure of the user from the information concerning event-related potential against a predefined criterion; and determining whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

Hereinafter, illustrative embodiments according to the present disclosure will be described.

First, the definitions of the terms used in the present specification will be described.

An "event-related potential (also denoted as ERP)" is a fluctuation in the potential of an electroencephalogram (EEG) that occurs in connection with a certain stimulation (event).

A "sound stimulation" is a stimulation which is presented to a user as a sound.

An "N1 component" is a negative potential which is induced at about 100 ms since the point of presenting a sound stimulation as a starting point.

A "P2 component" is a positive potential which is induced at about 200 ms since the point of presenting a sound stimulation as a starting point.

The N1 component and the P2 component are contained in an event-related potential.

"Latency" is the time, based on the point of presenting a sound stimulation as a starting point, until a peak potential of a positive component or a negative component appears. Note that a "peak potential of a positive component or a negative component" typically is a local maximum of a positive component or a local minimum of a negative component. A "peak potential" includes the maximum value of a positive component or the minimum value of a negative component.

A "negative component" generally refers to a potential which is smaller than 0 μV.

A "positive component" generally refers to a potential which is greater than 0 μV.

However, in a comparison between two potentials, the potential having the more negative value may be referred to as a negative component. Similarly, in a comparison between two potentials, the potential having the more positive value may be referred to as a positive component.

An "uncomfortable sound pressure (UCL)" is a sound pressure which is so loud that it is felt uncomfortable to a user.

A "hearing threshold level (also denoted as HTL)" is the sound pressure of a softest sound that is audible to a user, which may be referred to as an "auditory threshold value", or simply as a "threshold value".

"Presenting a sound" means outputting a pure tone.

A "pure tone" is a tone which repetitively undergoes periodic oscillation at a single frequency, such that it is expressed as a sine wave.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI— (or "Event-Related Potential (ERP) Manual—mainly concerning P300—"), edited by Kimitaka KALA et al., Shinohara Shuppan Shinsha, 1995)". Therefore, in the present specification, "about X ms" and "near X ms" are inclusive of a breadth of 30 to 50 ms before or after X ms (e.g., 100 ms±30 ms, 200 ms±50 ms).

Hereinafter, with reference to the attached drawings, embodiments of the uncomfortable sound pressure evaluation system according to the present disclosure will be described.

The uncomfortable sound pressure evaluation system according to the present disclosure allows a UCL which has been estimated as indexed by an electroencephalogram in response to a sound stimulation to be adjusted into an appropriate range on the basis of a distribution of measured UCLs. The inventors have found that an estimated UCL can be adjusted into an appropriate range by using UCLs which were measured in the experiments which the inventors performed for people suffering from hypacusia. The details will be described later. In the case where the uncomfortable sound pressure evaluation system according to the present disclosure is to be operated by an entity providing hearing aids, for example, UCLs which were measured by that entity or a body to which that entity belongs may instead be used. When hearing aid fitting is performed by using the adjusted UCL, overbearing sounds will not be presented, and consequently the user will not feel uncomfortable. Use of such a UCL is safe for a user who is new to a hearing aid, for example.

Hereinafter, prior to descriptions of the present disclosure, experiments conducted by the inventors, and the experimental results thereof, will be described. Moreover, a method of adjusting an estimated UCL devised by the inventors will be described. Thereafter, embodiments of the uncomfortable sound pressure evaluation system will be described in outline, together with their constructions and operations.

(Description of Experimental Outline)

1. Experimental Outline

The inventors have conducted the following two experiments for people suffering from hypacusia who were about to begin use of hearing aids, with a view to improving the accuracy of uncomfortable sound pressure estimation based on electroencephalograms.

First is a subjective report experiment of actually measuring a UCL based on subjective reporting. The subjective report experiment was conducted before an electroencephalogram measurement experiment (see below). UCL data which is obtained through a subjective report experiment is referred to as "a subjective UCL(s)". The inventors used the subjective UCLs as reference data for electroencephalogram estimation.

Second is an electroencephalogram measurement experiment of measuring electroencephalographic responses to sound stimulations. In the electroencephalogram measurement experiment, pure tones of the same frequency were presented totaling three times in succession, with monotonously-descending sound pressure changes of every 5 dB, and event-related potentials in response to the sound stimulations of first to third sounds were measured. Then, a UCL was estimated based on the event-related potentials. A UCL which is estimated based on electroencephalographic responses as an index will be referred to as an "estimated UCL".

Based on these results, the inventors have found that a UCL conforming to subjective reporting can be estimated even when presenting a sound stimulation of a sound pressure lower than a sound pressure which is generally evaluated to be the UCL for a person suffering from intermediate hypacusia, by applying linear discrimination to the electroencephalograms in response to the first to third sounds.

It is assumed that "a sound pressure lower than a sound pressure which is generally evaluated to be the UCL" may vary depending on the HTL. For example, FIG. 1 is a reported instance of UCLs predicted on the basis of HTL. This report is based on Pascoe, D. P. (1988), Clinical measurements of the auditory dynamic range and their relation to formulas for hearing aid gain, In Iensen. H. 1. (Ed.) Hearing Aid Fitting: Theoretical and Practical Views 13th Danavox Symposium. Copenhagen: Stougaard. In Embodiments of the present specification, any value that is lower by at least 5 dB or more than the predicted UCLs for different HTLs as shown in FIG. 1 is deemed as "a sound pressure lower than a sound pressure which is generally evaluated to be the UCL".

In order for an event-related potential to be induced by a sound stimulation, it is considered necessary that the sound pressure of the sound stimulation is higher than the HTL, because, unless the brain can recognize the sound stimulation, no electroencephalogram will be induced by that sound stimulation.

Therefore, in Embodiments of the present specification, "a sound pressure lower than a sound pressure which is generally evaluated to be the UCL" is defined as a sound pressure which is higher than the HTL and which is a range that is lower by at least 5 dB or more than the predicted UCLs for different HTLs as shown in FIG. 1. With this technique, a UCL estimation is achieved in a short time and with a high accuracy, without presenting overbearing sounds.

Hereinafter, the experiments conducted by the inventors and the results thereof, and characteristic features of electroencephalograms which have been found through their analysis will be described in detail.

(Description of Experimental Conditions)

2. Experiments

In order to study possibilities of UCL estimation based on ERP, estimated UCLs, which were estimated from ERP in response to sound stimulations, were compared against subjective UCLs which were actually measured through subjective reporting.

The subjects were 32 people suffering from hypacusia (27-83 years old, averaged at 71.5 years) who were about to begin use of hearing aids. Informed consent was obtained for participating in the experiments.

2-1. Subjective UCL Experiment

The inventors first measured HTLs, then subjective UCLs, and thereafter took electroencephalogram measurements. Subjective UCL measurements were taken under the following procedure.

By using an SPL audiometer (D2-36H, manufactured by DANA JAPAN), continuous sounds of 500 Hz, 1 kHz, 2 kHz, and 4 kHz were presented to one ear at a time by ascending method. It was asked that a hand be raised when they were felt too loud to hear, and these were recorded as subjective UCLs for each of the right or left ear and for each frequency.

Hereinafter, results of the subjective UCL experiment will be discussed. FIG. 2 shows auditory characteristics distributions concerning HTLs and subjective UCLs of all participants with respect to different frequencies, pooled regardless of the right or left ear. The horizontal axis represents HTL, and the vertical axis represents subjective UCL, both in units of dBSPL. The frequency value (500 Hz, 1 kHz, 2 kHz, 4 kHz) is indicated in the center above each distribution. At each lattice point, occurrence frequency is indicated by a circle symbol in a corresponding size.

It can be seen from FIG. 2 that UCL significantly fluctuates for the same HTL, especially when the HTL is 80 dBSPL or less. The maximum value of difference between subjective UCLs at the same frequency and same HTL is 50 dB. This indicates that each individual's interpretation of "unbearably loud" may significantly differ, thus making it difficult to universally estimate a subjective UCL from an HTL.

Together with the measurement results of HTL and subjective UCLs, FIG. 2 also shows an average UCL for each HTL according to Pascoe's aforementioned report (bold line), as converted in units of dBSPL. From the relative positioning between the bold line and the circles, it can be seen that the subjective UCLs of most participants are smaller than the UCLs which are predicted by the conventional study. Those subjective UCLs which exceed the UCL (bold line) predicted by the conventional study account only for 10.2% in total.

2-2. Electroencephalogram Measurement Experiment

In the electroencephalographic experiment, for each of four frequencies (500 Hz, 1000 Hz, 2000 Hz, 4000 Hz), sound stimulations were presented at three sound pressures (80, 75, 70 dBHL) lower than a sound pressure which is generally evaluated to be the UCL, successively at these monotonously descending sound pressures. In the present specification, three kinds of sound stimulations that are presented in such a manner will be referred to as "triplet sounds" or "triplet sound stimulations". Then, characteristic features of an event-related potential for each sound stimulation were studied. Hereinafter, with reference to FIG. 3 to FIG. 7, the experimental setting and experimental results of the electroencephalogram measurement experiment will be described.

FIG. 3 shows triplet sound stimulations in outline. As the sound stimulations, tone bursts with a rise/fall of 3 ms and a duration 44 ms were used. Three tone bursts of the same frequency (either 500 Hz, 1 kHz, 2 kHz, or 4 kHz) were successively presented to either the right or left ear with sound pressure decrements of every 5 dB from 80 dBHL, at an interval of 300 ms (triplet sounds; 3 frequencies×right or left=six conditions). The first sound, second sound, and third sound of the triplet sounds may be referred to as "S1", "S2", and "S3". Moreover, plural sound stimulations of the same frequency may also be referred to as a "sound stimulation group". The interval from the end of S3 to the beginning of S1 of the next triplet sounds was 450±50 ms. In order to reduce the influence of taming, it was ensured that no triplet sounds of the same frequency would follow. The triplet sounds were presented 80 times for each condition, totaling 640 times. The participants were instructed to silently listen to each sound that would be heard. No behavioral response was asked to be made.

The sound stimulations were output from a PC via headphones (HDA 200, manufactured by SENNHEISER). The sound pressures of the sound stimulations were calibrated by using a noise meter (LA-1440, manufactured by ONO SOKKI) and a coupler (IEC318, manufactured by Larson Davis).

By using active electrodes, the electroencephalogram was recorded from five positions on the scalp (Fz, Cz, Pz, C3, C4) as well as above the right eye and on the right of the right eye, on the basis of the right mastoid. A "mastoid" is a protrusion of the cranium below the hind root of an ear.

Figure 4B:
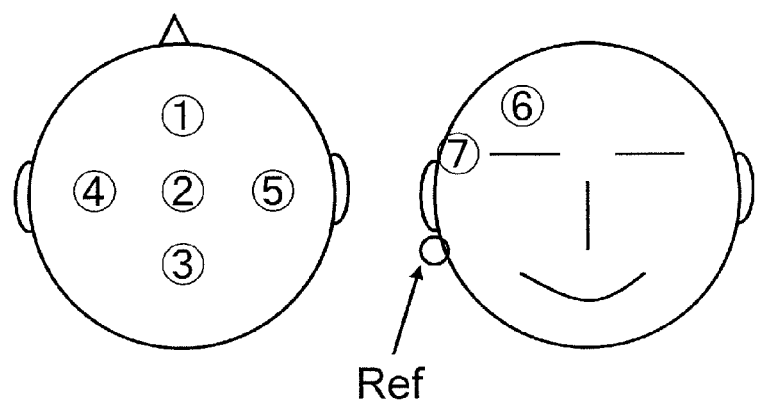
FIG. 4B is a diagram showing electrode positioning at which electrodes were worn in the present experiment.

FIG. 4A shows electrode positions according to the International 10-20 system (10-20 System). FIG. 4B shows the positions of electrodes worn in the present experiment. In FIG. 4B, circled numbers 1 to 5 represent electrode positions Fz, Cz, Pz, C3, and C4, respectively.

The sampling frequency was 1000 Hz; and the time constant was 1 second. Off-line, it was subjected to a 1-20 Hz band-pass filter. With the point of presenting S1 as a starting point, the span from −100 to 1000 ms was cut out, and an arithmetic mean was taken for each of the right or left ear and for each frequency to determine an ERP. Note that a point which is 1000 ms after the point of presenting S1 is synonymous to a point which is 400 ms after the point of presenting S3. Those trials which exhibited a potential exceeding ±80 µV at any electrode were excluded from the arithmetic mean. Moreover, in order to extract a time-frequency component contained in the electroencephalogram, a wavelet transform was applied to the electroencephalogram downsampled to 100 Hz. As the mother wavelet, the Mexican hat ($\phi(t)=(1-t^2)\exp(t^2/2)$) was used. The wavelet coefficients were scaled to integers from 1 to 9 (corresponding to 2.5-12.5 Hz). The wavelet coefficients were subjected to an arithmetic mean for each of the right or left ear and for each frequency, thus determining induced responses for the triplet sounds. The data of any frequency at which the HTL read greater than 70 dBHL, and one instance in which the electroencephalogram was not correctly measured, were excluded from the analysis.

Induced responses for the triplet sounds can be derived as a "wavelet characteristic amount". The inventors applied linear discrimination to the wavelet characteristic amount to estimate a UCL.

A wavelet characteristic amount is generated by, with the range from 0 to 900 ms of an arithmetic-meaned wavelet coefficient, taking an average in time windows of 50 ms for each scale. By combining two arbitrary wavelet characteristic amounts, the inventors learned correspondence between subjective UCLs and wavelet characteristic amounts in participants other than the subject himself or herself, which was then used as training data. The training data was pooled regardless of the right or left ear, and generated for each stimulation frequency.

Accuracy of UCL estimation was evaluated based on a mean error (an average of the absolute values of differences between subjective UCLs and estimated UCLs of all participants under analysis, for each of the right or left ear and for each frequency). A mean error was determined for every combination of wavelet characteristic amounts (totaling 13041 combinations).

Hereinafter, results of the electroencephalogram measurement experiment will be described.

First, in order to confirm that an index of uncomfortable sound pressure estimation is contained in the event-related potentials in response to changing sound pressures, not only in the results in Non-Patent Document 1 of people with normal hearing but also in people suffering from hypacusia, event-related potentials which were arithmetic-meaned based on subjective UCL were compared. In order to be able to estimate an uncomfortable sound pressure from an event-related potential, it is necessary that differences in event-related potential exist that reflect the subjective UCL of each participant.

Figure 5A:
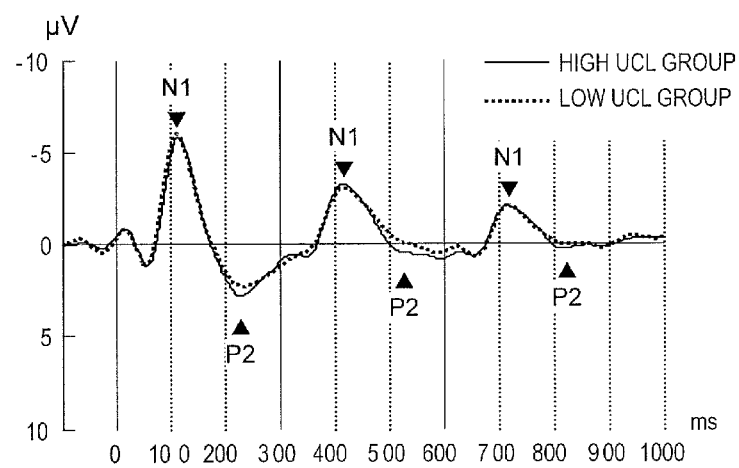
FIG. 5A is a diagram showing a total arithmetic mean waveform of event-related potentials recorded at the central portion (Cz), depending on whether the subjective UCL is high or low.
Figure 5B:
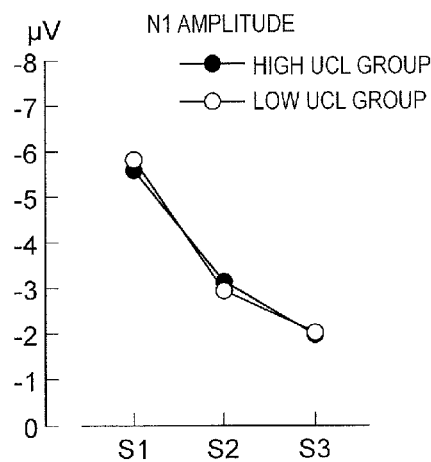
FIG. 5B is a diagram showing amplitude of an N1 component (N1 amplitude).
Figure 5C:
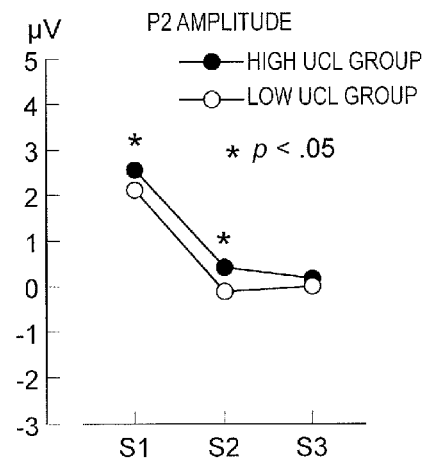
FIG. 5C is a diagram showing amplitude of a P2 component (P2 amplitude).

FIG. 5A shows a total arithmetic mean waveform of event-related potentials recorded at the central portion (Cz), depending on whether the subjective UCL is high or low. FIG. 5B shows amplitude of an N1 component (N1 amplitude), and FIG. 5C shows amplitude of a P2 component (P2 amplitude). In order to clarify the overall tendency for each subjective UCL, a total arithmetic mean was separately taken depending on whether the subjective UCL was high or low, with data being pooled regardless of the right or left ear and the frequency.

In FIG. 5A, the solid line represents a total arithmetic mean waveform of participants (high UCL group) whose subjective UCLs were higher than the average value of subjective UCLs for each frequency, and the broken line represents a total arithmetic mean waveform of participants (low UCL group) whose subjective UCLs were lower than the average value of subjective UCLs. The timing of presenting S1, S2, S3 (0, 300, 600 ms) is shown with each vertical solid line. Irrespective of whether the subjective UCL is high or low, after each sound stimulation presentation, a negative component (N1 component) is induced after about 100 ms, and a positive component (P2 component) after about 200 ms.

FIGS. 5B and 5C show N1 amplitude and P2 amplitude for respective sound stimulations. Through a t-test, no significant difference was recognized as to the N1 amplitude of FIG. 5B. On the other hand, the P2 amplitude of FIG. 5C showed a significant difference depending on whether the subjective UCL was high or low. Specifically, in the low UCL group, the P2 amplitudes were significantly smaller for S1 and S2 than in the high UCL group.

Figure 6:
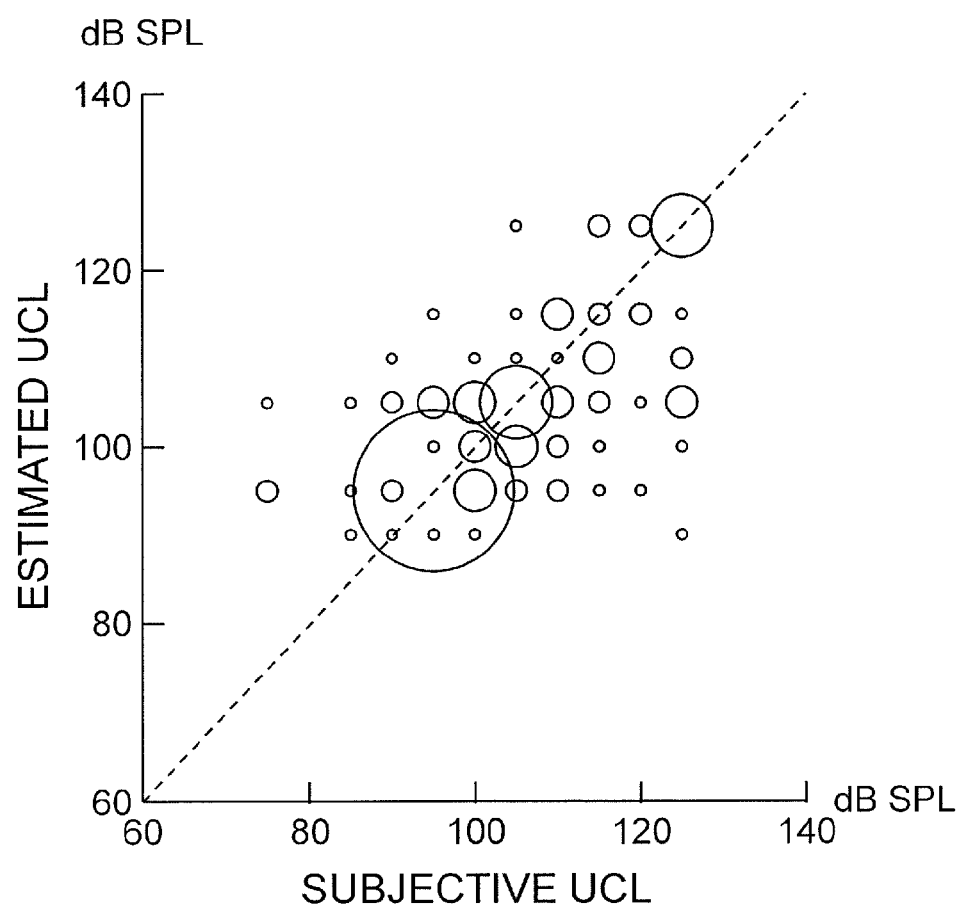
FIG. 6 is a diagram showing a distribution of results of UCL estimation through linear discrimination and subjective UCLs, pooled regardless of the right or left ear and the stimulation frequency.

FIG. 6 shows a distribution of results of UCL estimation through linear discrimination and subjective UCLs, pooled regardless of the right or left ear and the stimulation frequency. At each lattice point, occurrence frequency is indicated by a circle symbol in a corresponding size. The center of any circle being on the broken line means that a UCL which has been estimated through ERP analysis coincided with the actually-measured subjective UCL. Although there are fluctuations, many circles are at positions relatively near the broken line. Moreover, the center of the largest circle rests on the broken line. These indicate that the UCLs are estimated relatively accurately. There was a mean error of 7.0 dB. Note that the estimation error was 5 dB or less for 63.5% of the total population. The maximum estimation error was 35 dB.

As has been described above, it became clear through the subjective report experiment and electroencephalographic experiment conducted by the inventors that the event-related potential differs depending on whether the subjective UCL is high or low, such that the P2 amplitude for S1 and S2 appears smaller when the subjective UCL is low. Moreover, as a result of applying linear discrimination to the wavelet characteristic amount, the UCL was estimated with a mean error of 7.0 dB relative to the subjective UCL. These results suggest that UCL information is contained in the event-related potentials in response to triplet sounds, and that UCL estimation is possible through their analysis. Considering that the smallest graduation of a commonly-available audiometer is 5 dB, a mean error of 7.0 dB should be considered to be within tolerable errors in the measurements of auditory characteristics.

Figure 7:
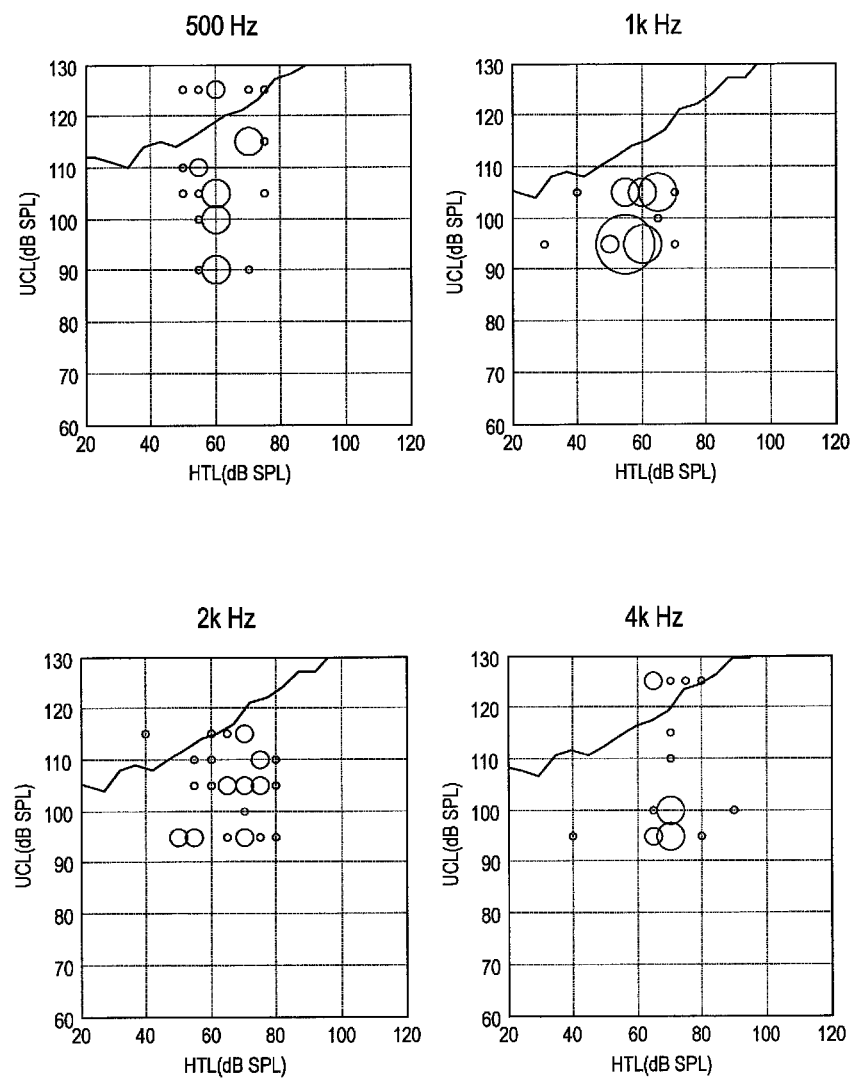
FIG. 7 shows diagrams showing a distribution of HTLs and estimated UCLs of all participants under analysis with respect to different frequencies, pooled regardless of the right or left ear.

FIG. 7 shows a distribution of HTLs and estimated UCLs of all participants under analysis with respect to different frequencies, pooled regardless of the right or left ear. The horizontal axis represents HTL, and the vertical axis represents estimated UCL, both in units of dBSPL. The frequency value (500 Hz, 1 kHz, 2 kHz, 4 kHz) is indicated in the center above each distribution. At each lattice point, occurrence frequency is indicated by a circle symbol in a corresponding size. Similarly to FIG. 2, the UCLs for different HTLs as predicted in Pascoe, D. P. (1988) are indicated by bold lines.

FIG. 7 indicates that, also in estimated UCLs, the UCL predicted by the conventional study (bold line) is exceeded in some cases. For example, if one looks at the cases of HTL=60 dBSPL among the 500 Hz results in FIG. 7, there is an increased occurrence frequency of estimated UCLs exceeding the UCL predicted by the conventional study, as compared to FIG. 2. One possible reason thereof is considered to be estimation errors. Therefore, when a hearing aid is adjusted by using an estimated UCL, there is a remote possibility that an overbearing sound that could be felt uncomfortable to the user may be presented from the hearing aid. The UCL predicted by the conventional study (bold line) being exceeded by an estimated UCL implies increased burden on the user.

Thus, from the subjective report experiment and electroencephalogram measurement experiment conducted by the inventors, it became clear that an uncomfortable sound pressure can be estimated from electroencephalographic responses to triplet sound stimulations, even among people suffering from hypacusia. While the mean error between subjective UCL and estimated UCL was 7.0 dB, there was a maximum error of 35 dB. In some cases, the estimation error induced a higher estimated UCL than the UCL predicted by the conventional study.

When limiting the number of sound stimulation presentations in an attempt to enable UCL estimation over a short time with little burden, the noises contained in the electroencephalogram make it difficult to reduce the estimation error to zero. Therefore, the present application provides a construction and operation for reducing the influence of significant estimation errors which rarely do occur. The specific operation thereof involves correcting an estimated UCL to a predetermined value when the estimated UCL is higher than a predetermined value which is defined for each HTL. The "predetermined value" may be value predicted by Pascoe (1988) for HTL as shown in FIG. 1, for example.

As shown in FIG. 2, in the subjective UCL experiment conducted by the inventors for users about to begin use of hearing aids, about 90% of the users showed subjective UCLs which were lower than the predicted values of Pascoe (1988). In other words, it can be said that any estimated value exceeding the predicted value of Pascoe (1988) is likely to contain a significant estimation error. Therefore, as one example, when an estimated UCL exceeds the predicted values of Pascoe (1988) defined for each HTL, the estimated UCL may be corrected so as to be equal to or less than the predicted value of Pascoe (1988), as set forth above.

As the aforementioned "predetermined value", the values reported in Keller. J. N (2006) Loudness discomfort levels: A retrospective study comparing data from Pascoe (1988) and Washington University School of Medicine, may instead be used.

FIG. 8 shows average UCLs for different HTLs, as reported by Keller (2006). When HTL is 20 dBHL or more, the UCL average values reported in Keller (2006) are lower than those of Pascoe (1988) by about 10 dB. With such corrections, even when a significant estimation error occurs, a safer hearing aid adjustment is realized.

Embodiment 1

Hereinafter, first, the uncomfortable sound pressure evaluation system will be described in outline. Thereafter, the construction and operation of an uncomfortable sound pressure evaluation system including the uncomfortable sound pressure evaluation apparatus will be described.

The uncomfortable sound pressure evaluation system according to the present embodiment extracts electroencephalographic characteristic amounts in response to sound stimulations, and estimates an uncomfortable sound pressure from a change pattern of the characteristic amounts. Then, the estimated uncomfortable sound pressure is compared against a predetermined value which is set for each HTL, and if the estimated uncomfortable sound pressure is greater than a predetermined value, the uncomfortable sound pressure is corrected to the predetermined value. On the other hand, if the estimated uncomfortable sound pressure is equal to or less than the predetermined value, correction is skipped, and the estimation result is accumulated.

In the present embodiment, by providing a probe electrode at the central portion (Cz) and a reference electrode at either the right or left mastoid, an electroencephalogram is measured as a potential difference between the probe electrode and the reference electrode. Note that the level and polarity of a characteristic component of the event-related potential may possibly vary depending on the sites at which electrodes for electroencephalogram measurement are worn, and on the positions at which the reference electrode and the probe electrode are set. However, based on the following description, those skilled in the art should be able to extract a characteristic feature of the event-related potential and perform estimation and correction of an uncomfortable sound pressure by making appropriate modifications in accordance with the particular reference electrode and probe electrode used. Such variants are encompassed within the present disclosure.

Figure 9:
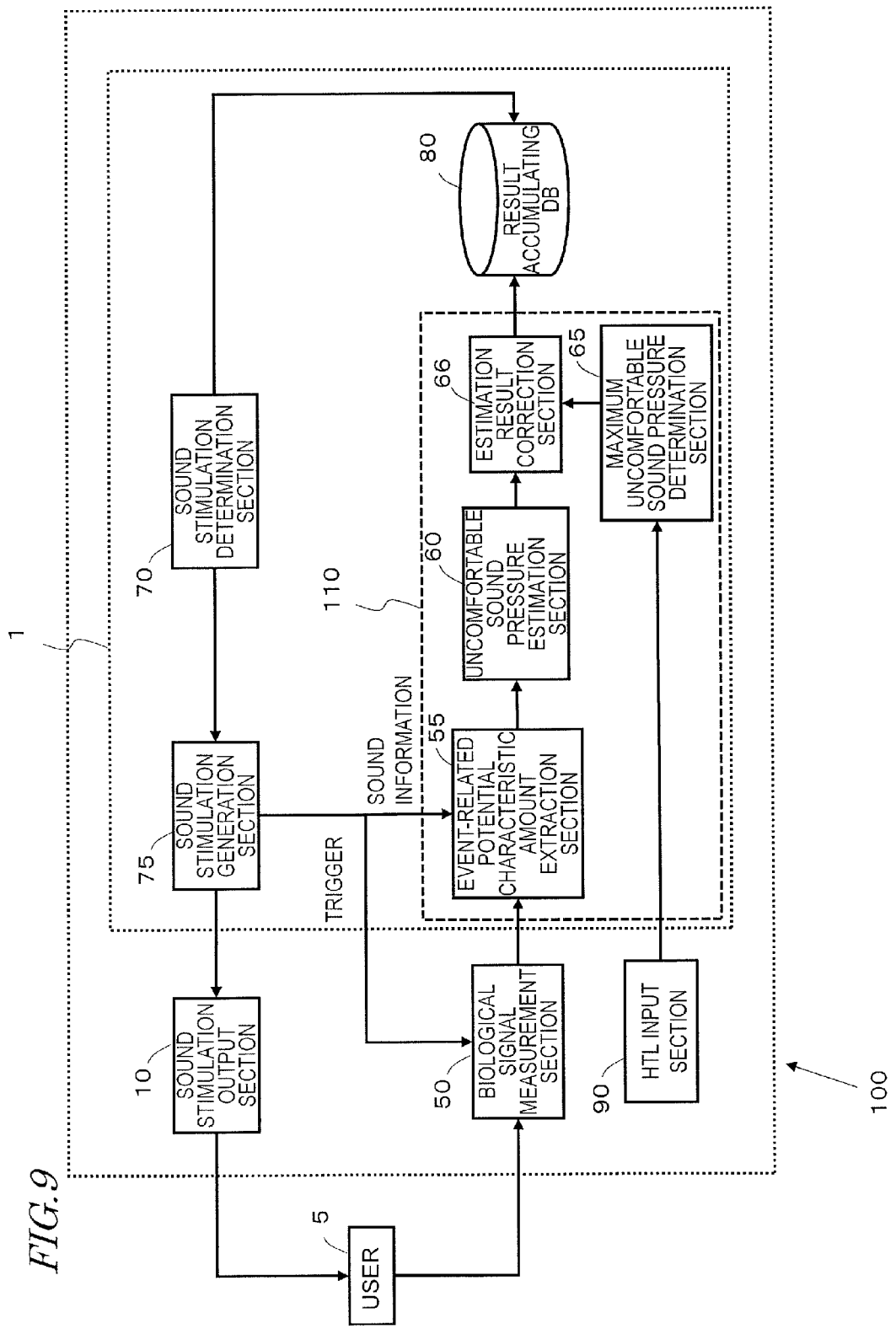
FIG. 9 is a construction diagram showing functional blocks of an uncomfortable sound pressure evaluation system 100 according to illustrative Embodiment 1.

FIG. 9 shows the functional block construction of the uncomfortable sound pressure evaluation system 100 according to the present embodiment. The uncomfortable sound pressure evaluation system 100 includes an uncomfortable sound pressure evaluation apparatus 1, a sound stimulation output section 10, a biological signal measurement section 50 (which hereinafter may also be referred to as the "measurement section 50"), and an HTL input section 90. Note that a user 5 is not a component element of the uncomfortable sound pressure evaluation system 100, but is illustrated for convenience of description.

The uncomfortable sound pressure evaluation apparatus 1 is connected in a wired or wireless manner to the sound stimulation output section 10, the measurement section 50, and the HTL input section 90, and mainly carries out the aforementioned operation of the uncomfortable sound pressure evaluation system.

The uncomfortable sound pressure evaluation apparatus 1 includes an event-related potential characteristic amount extraction section 55, an uncomfortable sound pressure estimation section 60, a maximum uncomfortable sound pressure determination section 65, an estimation result correction section 66, a sound stimulation determination section 70, a sound stimulation generation section 75, and a result accumulating database (DB) 80. The details of each component element and the operation of the uncomfortable sound pressure evaluation apparatus 1 will be specifically described later. Hereinafter, the event-related potential characteristic amount extraction section 55 may also be referred to as the "extraction section 55", the uncomfortable sound pressure estimation section 60 as the "estimation section 60", the estimation result correction section 66 as the "correction section 66", and the result accumulating DB 80 as the "DB 80".

The uncomfortable sound pressure evaluation apparatus 1 may at least include the extraction section 55, the estimation section 60, the maximum uncomfortable sound pressure determination section 65, and the correction section 66. These four component elements may be incorporated on a single semiconductor chip circuit, for example; in the present specification, such a semiconductor chip circuit may be referred to as the "uncomfortable sound pressure adjustment apparatus 110". Instead of a semiconductor chip circuit, it may be implemented by a CPU which is provided in a PC. By executing a computer program, the CPU is able to realize the function of each component element described below.

<Environment of Use>

Figure 10:
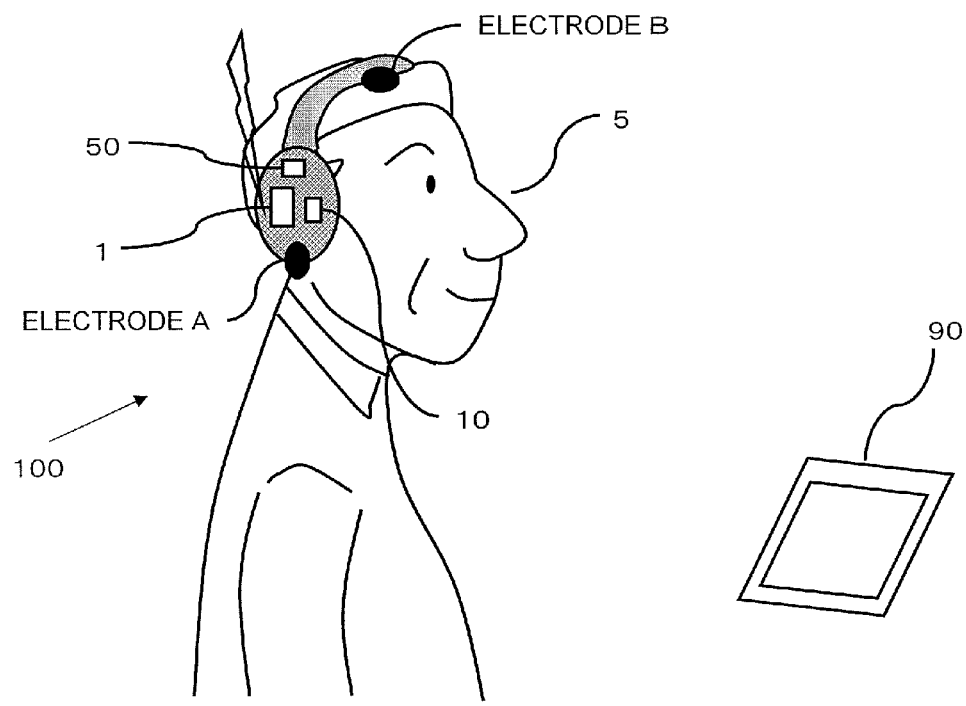
FIG. 10 is a diagram showing a construction and an environment of use for the uncomfortable sound pressure evaluation system 100 according to illustrative Embodiment 1.

FIG. 10 shows a construction and an environment of use for the uncomfortable sound pressure evaluation system 100 according to the present embodiment. The uncomfortable sound pressure evaluation system 100 corresponds to the system construction of Embodiment 1 shown in FIG. 9.

The uncomfortable sound pressure evaluation system 100 includes the uncomfortable sound pressure evaluation apparatus 1, the sound stimulation output section 10, the measurement section 50, and the HTL input section 90.

The HTL input section 90 is used for inputting an HTL of the user 5 which is measured in advance for each of the right or left ear and for each frequency. Inputting of the HTL may be done by the user 5, or by an entity which operates the uncomfortable sound pressure evaluation system 100, for example. When unit designation is possible, HTL may be in units of dBHL or dBSPL.

<Sound Stimulation Output Section 10>

The sound stimulation output section 10 outputs sound stimulations to the user 5.

The sound stimulation output section 10 allows sound stimulation data which is generated by sound stimulation generation section 75 (described later) of the uncomfortable sound pressure evaluation apparatus 1 to be presented as sound stimulations to the user 5. Preferably, the sound stimulation output section 10 allows sound stimulations generated by the uncomfortable sound pressure evaluation apparatus 1 (sound stimulation generation section 75) to be output to each of the right or left ear as correctly as possible. For example, the sound stimulation output section 10 may be headphones or a loudspeaker having little distortion in the frequency characteristics thereof. Hereinafter, the sound stimulation output section 10 may also be referred as the "output section".

<Biological Signal Measurement Section 50 (Measurement Section 50)>

The measurement section 50 is connected to at least two electrodes A and B. For example, electrode A is attached to a mastoid of the user 5, whereas electrode B is attached to a central portion (so-called Cz) on the scalp of the user 5. The measurement section 50 measures an electroencephalogram of the user 5 that corresponds to a potential difference between electrode A and electrode B.

The measurement section 50 is an electroencephalograph which measures a biological signal of the user 5. The measurement section 50 measures an electroencephalogram corresponding to a potential difference between a probe electrode and a reference electrode worn on the user 5.

The probe electrode is placed at an electrode position according to the International 10-20 system (10-20 System) shown in FIG. 4A, for example. The reference electrode is placed on a mastoid of the user 5, for example.

Note that the level (amplitude level) or polarity (plus or minus amplitude) the characteristic component of an event-related potential may possibly vary depending on the sites at which electrodes for electroencephalogram measurement are worn, and on the positions at which the reference electrode and the probe electrode are set.

However, based on the following description, those skilled in the art should be able to extract a characteristic feature of the event-related potential and perform estimation and correction of an uncomfortable sound pressure by making appropriate modifications in accordance with the particular reference electrode and probe electrode used. Such variants are encompassed within the present disclosure.

The resultant electroencephalogram data may be subject to frequency filtering with an appropriate cutoff frequency. The measurement section 50 sends the measured electroencephalogram or filtered electroencephalogram to the extraction section 55 of the uncomfortable sound pressure evaluation apparatus 1. Hereinafter, the measured electroencephalogram or filtered electroencephalogram may also be referred to as electroencephalogram data.

For example, the electroencephalogram data may be subjected to frequency filtering with an appropriate cutoff frequency, and together with trigger information which is received from the uncomfortable sound pressure evaluation apparatus 1 (sound stimulation generation section 75), it is sent to the extraction section 55 of the uncomfortable sound pressure evaluation apparatus 1.

In the case where a band-pass filter is used as the frequency filter, the cutoff frequency may be set so as to pass e.g. 1 Hz to 20 Hz. It is assumed that the user 5 has worn the electroencephalograph in advance. The probe electrode for electroencephalogram measurement is attached at the central portion Cz, for example.

<Uncomfortable Sound Pressure Estimation Apparatus 1>

The measurement section 50 and the sound stimulation output section 10 of the uncomfortable sound pressure evaluation apparatus 1 shown in FIG. 10 may be accommodated in the same housing. Alternatively, the measurement section and the sound stimulation output section 10 may be accommodated in a separate housing from that of the uncomfortable sound pressure evaluation apparatus 1. In that case, the measurement section 50 sends a measured electroencephalogram signal to the uncomfortable sound pressure evaluation apparatus 1 being connected in a wireless or wired manner. FIG. 10 illustrates the housing of the uncomfortable sound pressure evaluation apparatus 1 as being separate from the housing of the HTL input section 90. However, the uncomfortable sound pressure evaluation apparatus 1 and the HTL input section 90 may be accommodated within the same housing.

The uncomfortable sound pressure evaluation apparatus 1 determines the right or left ear, frequency, and sound pressure for the sound stimulations to be used in uncomfortable sound pressure estimation. Then, it generates the determined sound stimulations, and the sound stimulation output section 10 presents the sound stimulations determined by the uncomfortable sound pressure evaluation apparatus 1 to the user 5.

Moreover, from each event-related potential which has been cut out based on the sound stimulation as a starting point, the uncomfortable sound pressure evaluation apparatus extracts a characteristic amount for estimating an uncomfortable sound pressure, and based on a change pattern of the characteristic amounts with respect to changing sound pressures, determines an uncomfortable sound pressure for each of the right or left ear and for each frequency.

<Hardware Construction of the Uncomfortable Sound pressure evaluation apparatus 1>

Figure 11:
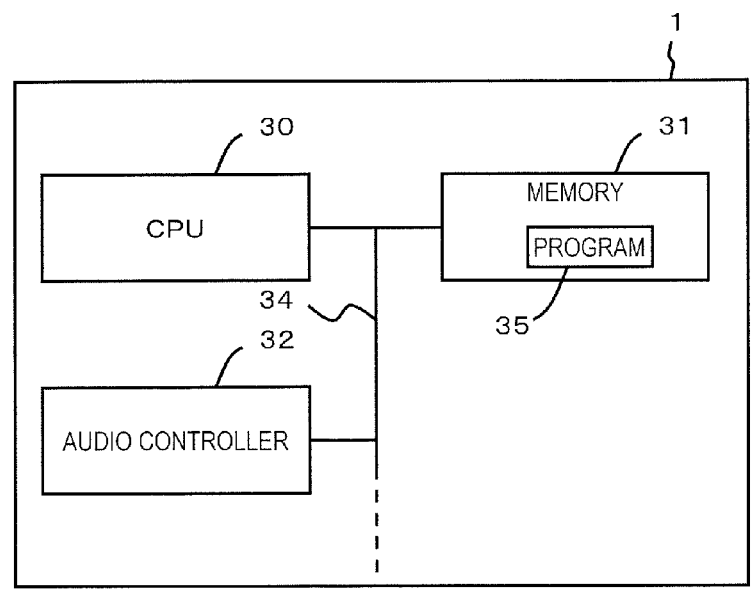
FIG. 11 is a diagram showing an exemplary hardware construction of the uncomfortable sound pressure evaluation apparatus 1 according to illustrative Embodiment 1.

FIG. 11 shows an exemplary hardware construction for the uncomfortable sound pressure evaluation apparatus 1 according to the present embodiment.

The uncomfortable sound pressure evaluation apparatus 1 includes a CPU 30, a memory 31, and an audio controller 32. The CPU 30, the memory 31, and the audio controller 32 are interconnected via a bus 34, so that data exchange among them is possible.

The CPU 30 executes a computer program 35 which is stored in the memory 31. A processing procedure as illustrated by a subsequently-described flowchart is described in the computer program 35. In accordance with the computer program 35, the uncomfortable sound pressure evaluation apparatus 1 performs processes to control the entire uncomfortable sound pressure evaluation system 100, e.g., sound stimulation generation, characteristic amount extraction from event-related potentials, and discriminant analysis for uncomfortable sound pressure determination. These processes will be described in detail later.

In accordance with instructions from the CPU 30, the audio controller 32 outputs the sound stimulations for presentation via the sound stimulation output section 10 at designated sound pressures.

Note that the uncomfortable sound pressure evaluation apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 11 (e.g., a PC) is able to function as the uncomfortable sound pressure evaluation apparatus 1 according to the present embodiment.

The respective functional blocks of the uncomfortable sound pressure evaluation apparatus 1 correspond to functions which are realized by the CPU 30, the memory 31, and the audio controller 32 as a whole upon executing the program which has been described in conjunction with FIG. 11.

Hereinafter, the respective component elements of the uncomfortable sound pressure evaluation apparatus 1 will be described.

<Sound Stimulation Determination Section 70>

The sound stimulation determination section 70 determines sound stimulations to be presented to the user 5. When successive sounds are to be presented as the sound stimulations, they are also referred to as a sound stimulation group. The sound stimulation determination section 70 outputs information of the sound stimulations.

Desirably, the sound stimulation group information contains the frequency of the sound stimulation group. In the case where the sound stimulation group is composed of a first sound, a second sound, and a third sound, it is desirable that the first sound, second sound, and third sound are at least of the same frequency. However, in the present specification, frequencies differing only so much that the differences are smaller than the precision of human hearing are regarded as the same frequency. In the present specification, for example, frequencies with a difference of Hz or less are regarded as the same frequency.

The sound stimulation group information may include the ear to which the sound stimulations are presented (right ear or left ear), the frequency of the presented sound stimulations, the duration of each sound stimulation in the sound stimulation group, and the interval between sound stimulations.

The ear to which the sound stimulation group is to be presented and the frequency thereof may be randomly decided under the following constraints, for example. No sound stimulation of the same frequency as that of an immediately previous sound stimulation group is selected. The right or left ear is preferably selected in random order. However, preferably, not more than four sound stimulation groups are successively presented to either the right or left ear alone. Thus, the influence of taming (habituation) of the electroencephalogram due to successive presentation of sound stimulation groups to the same ear and with the same frequency is reduced, whereby uncomfortable sound pressure estimation can be realized with a high precision.

The duration of a sound stimulation is set to be e.g. 25 ms or more, so that an auditory evoked potential is stably induced. The interval between stimulations is set to a time which is equal to or greater than the duration of the sound stimulation but equal to or less than 1 second. For example, it may be 300 ms, or 200 ms.

Moreover, the sound stimulation determination section 70 determines a sound pressure for the sound stimulation group having a sound pressure which is in a range equal to or less than a predetermined sound pressure, or which is equal to or less than a predetermined threshold value. A range equal to or less than a predetermined sound pressure may be, for example, a sound pressure range that is smaller than a common UCL. The sound stimulation determination section 70 may retain the predetermined range or predetermined threshold value in advance. For example, assuming that the predetermined threshold value is 90 dBHL, the sound pressure of the first sound may be determined to be 80 dBHL, the sound pressure of the second sound to be 75 dBHL, and the sound pressure of the third sound to be 70 dBHL.

Without being limited to successive sounds, a single sound stimulation may be presented to estimate a UCL as indexed by the amplitude of an N1 component of event-related potential. However, since a sound pressure at which the N1 component ceases to increase in spite of increasing sound pressure of the sound stimulations is deemed as the estimated UCL, it is necessary to present a sound stimulation of a sound pressure exceeding the subjective UCL. Therefore, the sound stimulations are to be presented at sound pressures within a predetermined range that is based on the HTL-by-HTL UCLs reported by Pascoe (1988).

Alternatively, two sound stimulations may be presented in succession, and a UCL may be estimated as indexed by the amplitude of a P2 component of event-related potential. For example, a P2 component based on the point of presenting each sound may be utilized.

The sound stimulation determination section 70 sends the determined sound stimulation information to the sound stimulation generation section 75.

<Sound Stimulation Generation Section 75>

The sound stimulation generation section 75 receives information concerning sound stimulations from the sound stimulation determination section 70, and generates sound stimulation data. The sound stimulation generation section outputs the sound stimulation data to the sound stimulation output section 10. This sound stimulation data is a piece of data for outputting sound stimulations. In the present specification, each sound stimulation may be a tone burst sound with a rise and fall of 3 ms, for example. The sound stimulation data generated by the sound stimulation generation section 75 is presented to the user 5 as sound stimulations via the sound stimulation output section 10.

At the timing that each sound stimulation is output, the sound stimulation generation section 75 outputs a trigger signal to the measurement section 50, and outputs sound information to the extraction section. The sound information is information concerning the generated sound stimulation data. The sound information may contain information of the ear to which the sound stimulation group is to be presented and its frequency, and the duration, stimulation interval, and sound pressures of the sound stimulations in the sound stimulation group, for example.

Note that the sound stimulation generation section 75 may only send generated sound stimulation data to the sound stimulation output section 10.

The sound stimulation data may be data which contains, for one sound stimulation group, plural sound stimulations that undergo changes in sound pressure at a predetermined time interval, for example. In other words, it is not necessary for sound stimulation data to be generated for each single sound stimulation. In that case, the trigger signal to be sent to the measurement section 50 may only be sent at the timing of presenting the first sound.

Note that the sound stimulation generation section 75 may be constituted as an input section. Information which is input by the user 5 or a person who tests the hearing of the user 5 via the input section may be utilized as information of auditory stimulations.

<Event-Related Potential Characteristic Amount Extraction Section 55 (Extraction Section 55)>

The extraction section 55 acquires the electroencephalogram and trigger information received from the measurement section 50. In the present embodiment, the timing of receiving trigger information corresponds to the point of presenting a sound stimulation. Within the electroencephalogram, an event-related potential is to be acquired from a zone which is a predetermined time after the point indicated in the trigger information. A "zone which is a predetermined time after . . . " means a zone from 100 ms before presenting the first sound until 400 ms after presenting the third sound, for example.

The extraction section 55 extracts information concerning event-related potential. More specifically, the extraction section 55 acquires from the measurement section 50 event-related potentials which are induced by the first sound, second sound, and third sound being presented, and extracts information concerning these event-related potentials.

Moreover, the extraction section 55 acquires sound information from the sound stimulation generation section 75. Based on the sound information received from the sound stimulation generation section 75 and in accordance with the particulars of the sound stimulations, e.g. when successive sounds are to be presented as sound stimulations, the extraction section 55 may respectively calculate time frequency information (characteristic amounts) of the event-related potentials corresponding to the first to third sounds.

An event-related potential is a fluctuation in the potential of an electroencephalogram that occurs in response to a stimulation. The event-related potential comes in different event-related potential types, depending on: (1) the polarity of potential (plus or minus); (2) the latency (the time from occurrence of a stimulation until occurrence of a potential fluctuation); (3) the amplitude level of potential; and so on. Each different type of signal contains different information concerning the user 5. The N1 component and the P2 component as referred to in the present embodiment are electroencephalogram components appearing in time slots which are about 100 ms apart; it is well known in the field of event-related potential that these components are distinct from each other. It is also well known in the field of event-related potential that the N1 component and the P2 component are distinct from the so-called P3 component, for example.

An example of time frequency information is wavelet coefficients. Moreover, time frequency information may be calculated through short-time Fourier transform.

The extraction section 55 sends the calculated characteristic amount and the sound stimulation information (right or left ear, frequency, sound pressure, etc.) to the estimation section 60. The wavelet-coefficient related characteristic amount may be a value calculated by averaging the wavelet coefficients in a predetermined range on each of the frequency axis and the time axis, for example. For instance, an average of wavelet coefficients may be calculated across 5 Hz to 15 Hz on the frequency axis and in a time range of every 50 ms on the time axis.

Furthermore, as a P2 component of event-related potential for characteristic amount calculation, for example, a biological signal in a time range from the point of presenting an auditory stimulation until 300 ms or less after the auditory stimulation may be used. The breadths of averaging on the frequency axis and the time axis for characteristic amount calculation may be finer or coarser than 5 Hz to 15 Hz and every 50 ms, so long as an uncomfortable sound pressure can be estimated.

Alternatively, as a P2 component of event-related potential for characteristic amount calculation, for example, a biological signal with a positive component in a time range from no less than 150 ms to no more than 250 ms after presenting an auditory stimulation may be used. For example, as an N1 component of event-related potential for characteristic amount calculation, a biological signal with a negative component in a time range from no less than 50 ms to no more than 150 ms after presenting an auditory stimulation may be used.

<Uncomfortable Sound Pressure Estimation Section 60 (Estimation Section 60)>

The estimation section 60 estimates an uncomfortable sound pressure of the user 5 by referring to the characteristic amount for each sound stimulation (e.g., a wavelet coefficient(s)) extracted by the extraction section and a predetermined criterion which previously defines associations between characteristic amounts and uncomfortable sound pressure values. In the present specification, "to estimate" is synonymous with "to determine".

Specifically, the estimation section 60 determines an uncomfortable sound pressure given the characteristic amount for each sound stimulation (e.g., respective wavelet coefficients for the first to third sounds) received from the extraction section 55. In the estimation section 60, linear discrimination is performed by using the characteristic amounts prepared in advance and the predetermined criterion.

The "predetermined criterion" means information which previously defines associations between characteristic amounts and uncomfortable sound pressure values. The "predetermined criterion" may be a table or a predetermined equation which defines associations between wavelet characteristic amounts and uncomfortable sound pressure values. The estimation section 60 retains the predetermined criterion in advance. Alternatively, the "predetermined criterion" may be training data for subjective UCLs, for example. The training data can be generated from subjective UCLs and wavelet characteristic amounts previously measured by conducting the aforementioned subjective report experiment and electroencephalogram measurement experiment for at least two more other people.

The sound stimulation conditions concerning the sound pressures and number of sound stimulations in the electroencephalogram measurement experiment when generating the training data need to identically conform to the pattern of changing stimulation sound pressure as determined by the sound stimulation determination section 70, in the case where successive sounds are presented as the sound stimulations. The training data may be retained so as to be itemized for each of the right or left ear and for each frequency, as shown in FIG. 7, for example. In that case, based on the sound information received from the extraction section 55 (e.g., information of the right or left ear to which the sound stimulations are presented and sound stimulation frequency), the training data which is utilized for uncomfortable sound pressure estimation may be switched so that the right or left ear and frequency of the one who is the subject of determination match the right or left ear and frequency of the training data. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss. The estimation section 60 sends the determined uncomfortable sound pressure to the correction section 66.

<Maximum Uncomfortable Sound Pressure Determination Section 65>

The maximum uncomfortable sound pressure determination section 65 receives an HTL for each frequency from the HTL input section 90, and determines a maximum uncomfortable sound pressure for each frequency. The "maximum uncomfortable sound pressure" means a maximum value of uncomfortable sound pressure that is defined based on the relationship with that user 5. As the grounds for being able to determine a maximum uncomfortable sound pressure from an HTL, which is the smallest audible level, the present disclosure relies on the established assumption that associations can be defined between HTLs and maximum uncomfortable sound pressures. The maximum uncomfortable sound pressure determination section 65 may receive an HTL for each of the right or left ear of the user 5, and determine a maximum uncomfortable sound pressure for each of the right or left ear.

The maximum uncomfortable sound pressure determination section 65 retains in advance a predetermined criterion which defines associations between HTLs and maximum uncomfortable sound pressures for each frequency. For example, the predetermined criterion is information which defines associations between HTLs and maximum uncomfortable sound pressures as determined based on means other than electroencephalogram, e.g., subjective reporting.

Based on the HTL, the predetermined criterion may dictate that a corresponding predicted value of Pascoe (1988) shown in FIG. 1, or a corresponding value which is reported in Keller (2006) shown in FIG. 8 is the maximum uncomfortable sound pressure. Specifically, 110 dBHL may be selected when the HTL is 60 dBHL, for example.

These values may be switched based on the experience of wearing a hearing aid. It is generally considered that, through experiences of wearing hearing aids, one becomes accustomed to loud sounds, thus reaching a higher subjective UCL. Therefore, Pascoe's values (1988) may be applied for those who have experienced a hearing aid, and Keller's values (2006) for those who have never experienced a hearing aid.

As described above, the "predetermined criterion" includes information of maximum uncomfortable sound pressure. Therefore, the maximum uncomfortable sound pressure determination section 65 can be considered as a storage device storing predefined maximum uncomfortable sound pressures.

<Estimation Result Correction Section 66 (Correction Section 66)>

The correction section 66 compares the maximum uncomfortable sound pressure for each of the right or left ear and for each frequency as received from the maximum uncomfortable sound pressure determination section 65 against the estimated UCL received from the estimation section 60 to determine whether the estimated UCL is the higher. If the estimated UCL is higher than the maximum uncomfortable sound pressure, the estimated UCL is corrected to the maximum uncomfortable sound pressure. This correct UCL is referred to as the "corrected UCL". On the other hand, if the estimated UCL is lower than the maximum uncomfortable sound pressure, no correction is made. The correction section 66 sends the corrected UCL or the estimated UCL to the DB 80.

Figure 12:
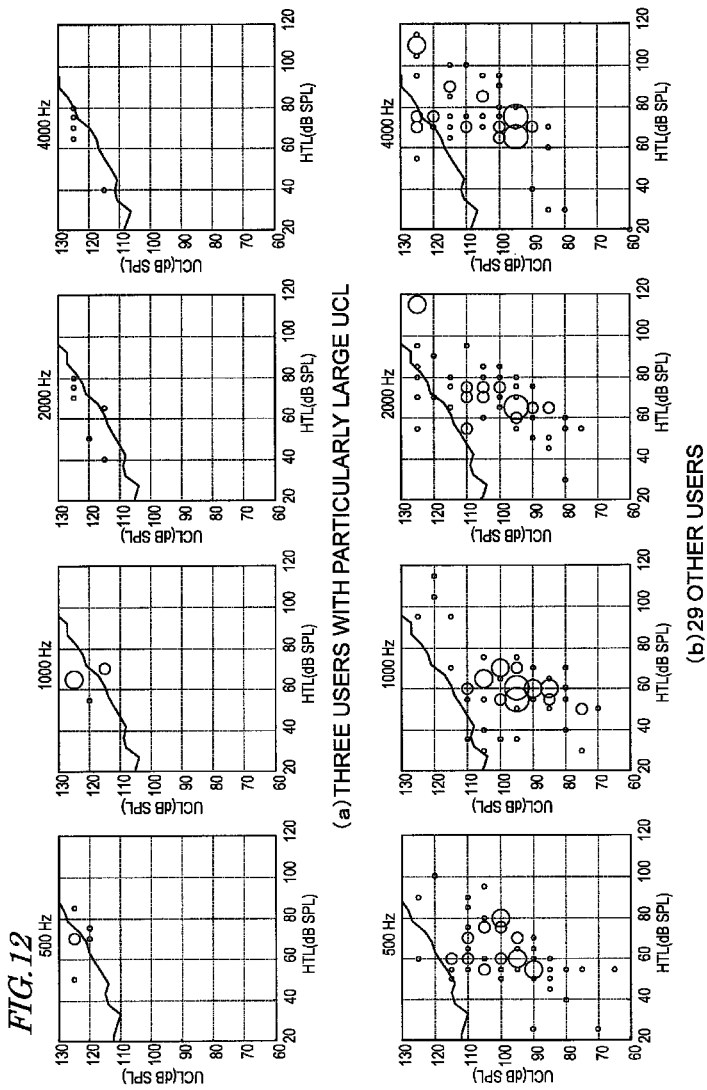
FIG. 12 shows diagrams showing distributions of HTLs and subjective UCLs of all of the participants shown in FIG. 2.

FIGS. 12(a) and (b) show distributions of HTLs and subjective UCLs of all of the participants shown in FIG. 2. FIG. 12(a) shows distributions of three people who showed particularly large subjective UCLs relative to the HTL-by-HTL UCLs according to Pascoe (1988). FIG. 12(b) shows distributions of 29 others. Similarly to FIG. 2, the horizontal axis represents HTL, and the vertical axis represents subjective UCL, both in units of dBSPL. From the left, results for 500 Hz, 1 kHz, 2 kHz, 4 kHz are respectively shown. At each lattice point, occurrence frequency is indicated by a circle symbol in a corresponding size.

From FIG. 12(a) it can be seen that users with high subjective UCLs are characterized by high overall subjective UCLs, irrespective of frequency. Concerning the results of 29 people shown in FIG. 12(b), the relationship between the bold lines and the circles indicates that the UCLs of most participants are lower than the UCLs predicted by conventional studies. In fact, it was among 4.0% (or 10.2% in total as mentioned earlier) that the subjective UCL exceeded the UCLs predicted by conventional studies (bold line).

Therefore, if the estimated UCL for each of the right or left ear and for each frequency as received from the estimation section 60 is greater than the maximum uncomfortable sound pressure for a half or more of the frequencies, for example, the correction section 66 may determine the user to be a user with a high uncomfortable sound pressure, and abstain from correcting the estimation result.

It can be seen from FIG. 2 that UCL significantly fluctuates for the same HTL, especially when the HTL is 80 dBSPL or less. The maximum value of difference between subjective UCLs at the same frequency and same HTL is 50 dB. This indicates that each individual's interpretation of "unbearably loud" may significantly differ, thus making UCL measurement through subjective reporting difficult.

<Result Accumulating DB 80 (DB 80)>

The DB 80 stores the uncomfortable sound pressures (corrected UCLs or estimated UCLs) received from the correction section 66. At this time, based on the sound stimulation group information received from the sound stimulation determination section 70, the DB 80 stores an uncomfortable sound pressure for each of the right or left ear and for each frequency. FIG. 13 shows an example of data accumulation in the DB 80. FIG. 13 illustrates a case where an uncomfortable sound pressure for each of the right or left ear and for each frequency is to be accumulated.

<Processing by the Uncomfortable Sound Pressure Evaluation System 100>

Figure 14:
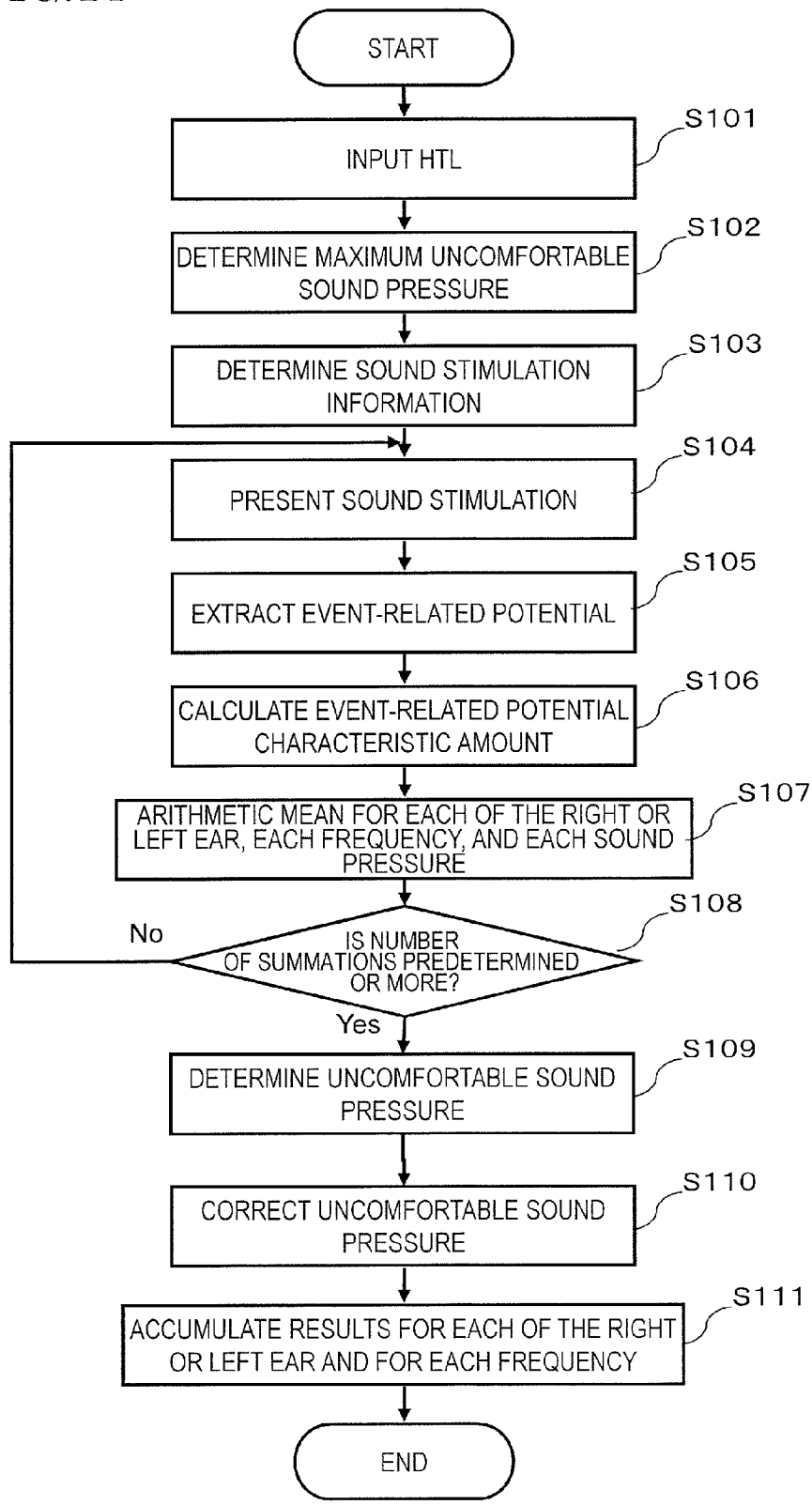
FIG. 14 is a flowchart showing a procedure of processing performed in the uncomfortable sound pressure evaluation system 100.

Next, with reference to FIG. 14, the procedure of processing performed by the uncomfortable sound pressure evaluation system 100 of FIG. 9 will be described. FIG. 14 is a flowchart showing a procedure of processing performed in the uncomfortable sound pressure evaluation system 100.

At step S101, the HTL input section 90 receives an input of HTL of the user 5 as measured in advance for each of the right or left ear and for each frequency. When unit designation is possible, HTL may be in units of dBHL or dBSPL.

At step S102, the maximum uncomfortable sound pressure determination section 65 receives an HTL of the user 5 for each of the right or left ear and for each frequency from the HTL input section 90, and determines a maximum uncomfortable sound pressure for each of the right or left ear and for each frequency. As one example, in the present embodiment, the maximum uncomfortable sound pressure is determined to be a predicted value of Pascoe (1988) shown in FIG. 1 or a value reported by Keller (2006) shown in FIG. 8, based on the HTL. Specifically, 110 dBHL may be selected when the HTL is 60 dBHL, for example.

At step S103, the sound stimulation determination section 70 determines information of plural sound stimulations to be presented to the user 5. Plural sound stimulations which are successively presented are also referred to as a "sound stimulation group". The sound stimulation group information contains the ear to which the sound stimulations are presented (right ear or left ear), the frequency of the presented sound stimulations, the duration of each sound stimulation in the sound stimulation group, and the interval between plural sound stimulations.

The ear to which the sound stimulation group is to be presented and the frequency thereof may be randomly decided under the constraint that no sound stimulation of the same frequency as that of an immediately previous sound stimulation group is selected, for example. The right or left ear is preferably selected in random order. However, preferably, not more than four sound stimulation groups are successively presented to either the right or left ear alone. Thus, the influence of taming (habituation) of the electroencephalogram due to successive presentation of sound stimulation groups to the same ear and with the same frequency is reduced, whereby uncomfortable sound pressure estimation can be realized with a high precision.

The duration of a sound stimulation is set to be e.g. 25 ms or more, so that an auditory evoked potential is stably induced. For example, the stimulation interval is set to be an amount of time from no less than 100 ms to no more than 1 s.

Moreover, the sound stimulation determination section 70 determines the sound pressures of the first to third sounds in the sound stimulation group so as to be in a sound pressure range which is smaller than is generally considered to be the UCL, e.g., 80 dBHL, 75 dBHL, and 70 dBHL. Then, the sound stimulation determination section 70 sends the determined sound stimulation information to the sound stimulation generation section 75.

At step S104, the sound stimulation generation section 75 generates sound stimulation data containing information of the ear to which the sound stimulation group is to be presented and its frequency, and the duration, stimulation interval, and sound pressures of the sound stimulations in the sound stimulation group as received from the sound stimulation determination section 70. Each sound stimulation may be a tone burst sound with a rise and fall of 3 ms, for example. Then, the sound stimulations are output to the user 5 via the sound stimulation output section 10. At the timing that the sound stimulations are output, the sound stimulation generation section 75 outputs a trigger signal to the measurement section 50.

For example, the sound stimulation generation section 75 may generate a piece of sound stimulation data which contains, for one sound stimulation group, plural sound stimulations that undergo changes in sound pressure at a predetermined time interval. In that case, the trigger signal to be sent to the measurement section 50 may only be sent at the timing of presenting the first sound. Note that the sound stimulation generation section 75 may generate the information sound stimulation data based on information which is not from the sound stimulation determination section 70, but is input from an input device (not shown). Information of the ear to which the sound stimulation group is to be presented and its frequency, and the duration, stimulation interval, and sound pressures of the sound stimulations in the sound stimulation group which is input by the user 5 or a person who tests the hearing of the user 5 via the input device may be utilized as information of auditory stimulations.

At step S105, the measurement section 50 measures an electroencephalogram of the user 5 as a biological signal, and sends the resultant electroencephalogram data to the extraction section 55. It is assumed that the measurement section 50 continues electroencephalogram measurement and keeps sending the electroencephalogram data to the extraction section 55 until step S111 is ended. When a trigger is input to the measurement section 50, the measurement section 50 sends the electroencephalogram data, including the trigger information, to the extraction section 55.

At step S106, based on the electroencephalogram data and trigger information received from the measurement section 50, the extraction section 55 cuts out from the electroencephalogram data event-related potential data in a predetermined zone based on the trigger information as a starting point (e.g., a zone from 100 ms before presenting the first sound until 400 ms after presenting the third sound). Then, in accordance with the particulars of sound stimulations received from the sound stimulation generation section 75, the extraction section 55 calculates respective wavelet-coefficient related characteristic amounts for the first to third sounds.

At step S107, based on the sound stimulation information received from the sound stimulation determination section 70, the extraction section 55 takes an arithmetic mean of the wavelet coefficient calculated at step S106, for each of the right or left ear and for each frequency.

At step S108, the extraction section 55 determines whether the number of summations for taking an arithmetic mean of the sound stimulations of the sound stimulation group presented at step S104 has reached a predetermined number of times or not. If the number of summations for arithmetic mean is smaller than the predetermined number of times, the process returns to step S103, and presentation of the sound stimulation group is repeated. If the number of summations for arithmetic mean is equal to or greater than the predetermined number of times, the extraction section 55 sends the arithmetic-meaned wavelet-coefficient related characteristic amount to the estimation section 60, and the process proceeds to step S109. The predetermined number of times may be 20 times, for example. Note that "20 times" is a mere example, although it is a number of summations which is frequently adopted in fields where event-related potentials are to be measured.

At step S109, the estimation section 60 determines an uncomfortable sound pressure by utilizing the respective wavelet-coefficient related characteristic amounts for the first to third sounds which have been received from the extraction section 55. The uncomfortable sound pressure determination is realized through linear discrimination, utilizing training data of wavelet characteristic amounts and subjective UCLs of other people which are prepared in advance.

The training data used for uncomfortable sound pressure estimation may be switched so that the right or left ear and frequency of the one who is the subject of determination match the right or left ear and frequency of the training data. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss. Then, the result of uncomfortable sound pressure determination is sent to the correction section 66.

At step S110, the correction section 66 compares the maximum uncomfortable sound pressure for each of the right or left ear and for each frequency as received from the maximum uncomfortable sound pressure determination section 65 against the estimated UCL received from the estimation section 60 to determine whether the estimated UCL is the higher. If the estimated UCL is higher than the maximum uncomfortable sound pressure, the estimated UCL is corrected to the maximum uncomfortable sound pressure, thus obtaining a corrected UCL. On the other hand, if the estimated UCL is lower than the maximum uncomfortable sound pressure, no correction is made. The correction section 66 sends the corrected UCL or the estimated UCL to the DB 80.

Note that the correction section 66 may determine whether the estimated UCL for each of the right or left ear and for each frequency as received from the estimation section 60 is greater than the maximum uncomfortable sound pressure or not, and if the estimated UCL is greater than the maximum uncomfortable sound pressure for a predetermined proportion (e.g. a half or more) of the frequencies, determine the user to be a user with a high uncomfortable sound pressure, and abstain from correcting the estimation result. Stated otherwise, the correction section 66 may determine whether the estimated UCL for each of the right or left ear and for each frequency as received from the estimation section 60 is greater than the maximum uncomfortable sound pressure or not, and abstain from correcting the estimation result if the determination results saying that the estimated UCL is higher than the maximum uncomfortable sound pressure account for a predetermined proportion or greater. On the other hand, if the determination results saying that the estimated UCL is higher than the maximum uncomfortable sound pressure account for a proportion that is smaller than a predetermined value, then the correction section 66 may, with respect to each estimated UCL that has been determined as higher than the maximum uncomfortable sound pressure, correct the estimated UCL to the maximum uncomfortable sound pressure and output it.

At step S111, for each of the right or left ear and for each frequency of the sound stimulation group presented at step S104, the DB 80 accumulates information of the corrected UCL received from the correction section 66.

Among the aforementioned steps, the steps that are executed by the uncomfortable sound pressure adjustment apparatus 110 are from steps S105 to S110. In other words, the uncomfortable sound pressure evaluation system 100 according to the present embodiment may at least execute steps S105 to S110, while the other processes are not essential.

With the uncomfortable sound pressure evaluation system 100 of the present embodiment, based on a distribution of actually-measured UCLs acquired from the user, a UCL which has been estimated as indexed by an electroencephalogram in response to a sound stimulation is adjusted into an appropriate range. This realizes a safe hearing aid fitting which does not hurt the user's ear by presenting an overbearing sound when adjusting the hearing aid with an estimated UCL.

In the description of the present embodiment, it is illustrated that the measurement section 50 cuts out an event-related potential in a predefined range based on a trigger from the sound stimulation generation section 75 as a starting point, and sends it to the extraction section 55. However, this process is an example. In another process, for example, the measurement section 50 may constantly measure an electroencephalogram, and the extraction section 55 may performing cutting out of an event-related potential and a baseline correction as needed. With such a construction, the sound stimulation generation section 75 does not need to send a trigger to the measurement section 50, but may only send a trigger to the extraction section 55.

Although the present embodiment illustrates that the estimated UCLs and the corrected results of uncomfortable sound pressure are accumulated in the DB 80, accumulation is not necessary. For example, in the case where the DB 80 is provided external to the uncomfortable sound pressure evaluation apparatus 1, each result of the correction section 65 may simply be output.

Additional construction may be introduced to allow an adjuster of the hearing aid or the like to have information as to whether a correction has indeed been made when the estimated UCL is corrected to or below the maximum uncomfortable sound pressure. For example, when the correction section 66 accumulates information of a corrected uncomfortable sound pressure in the DB 80, a flag indicating that it has been corrected, or a piece of data indicating whether or not it has been corrected, may be recorded in association with that uncomfortable sound pressure. For example, when the adjuster of the hearing aid makes use of an uncomfortable sound pressure that is accumulated in the DB 80, a hearing aid adjustment system of the hearing aid adjuster may rely on the presence or absence of such a flag to display any corrected uncomfortable sound pressure in a different color from that of an estimated UCL on a monitor. This allows the adjuster of the hearing aid to know whether a correction has been made or not. Each determination result is available for use as information concerning the uncomfortable sound pressure.

Embodiment 2

From a change pattern in uncomfortable sound pressure estimation values for each of the right or left ear and for each stimulation frequency during uncomfortable sound pressure measurement, an uncomfortable sound pressure evaluation system according to the present embodiment determines whether a result of uncomfortable sound pressure estimation may exceed a maximum uncomfortable sound pressure or not, and if the maximum uncomfortable sound pressure is likely exceeded, then ends uncomfortable sound pressure measurement for that stimulation.

Figure 15:
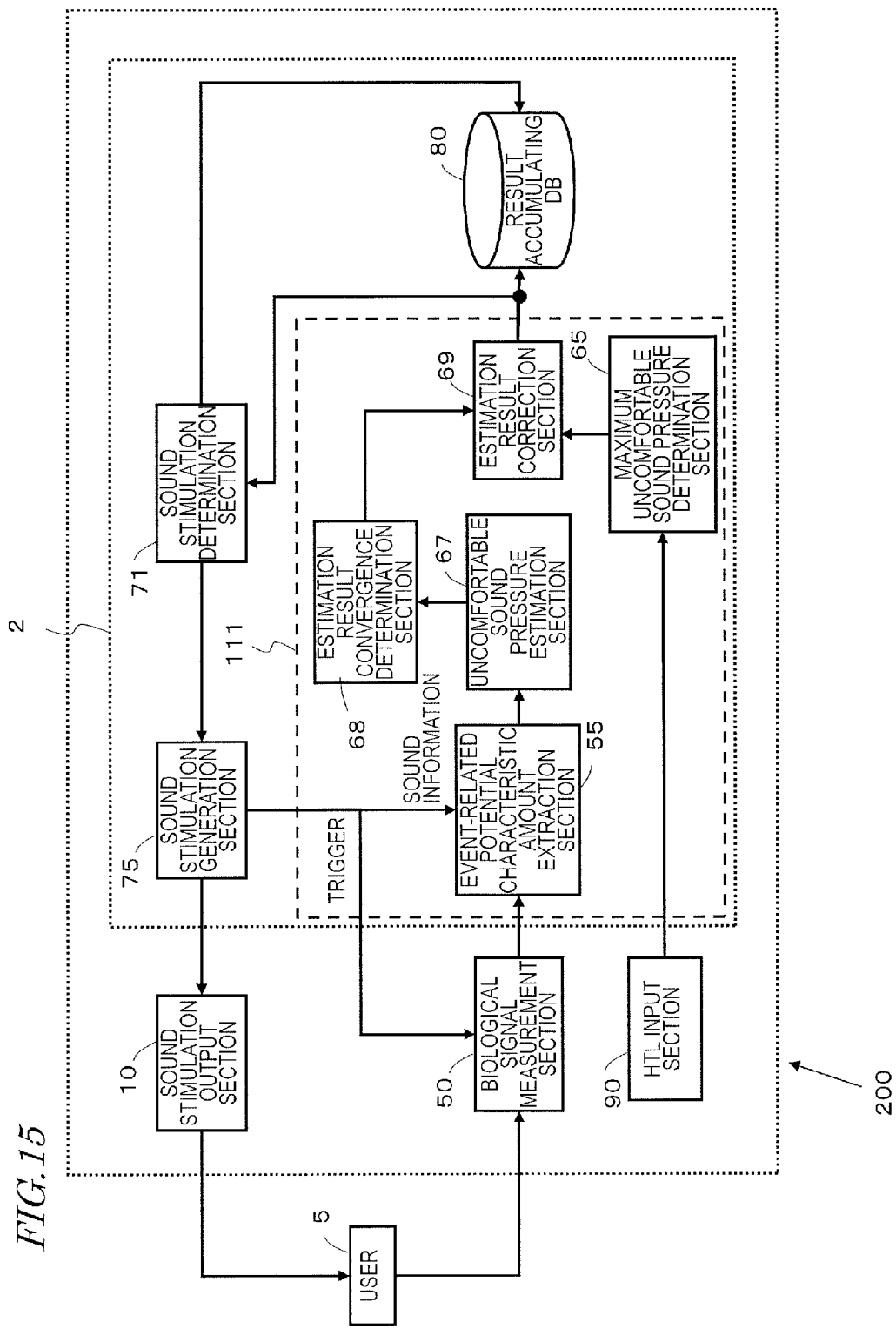
FIG. 15 is a diagram showing the functional block construction of an uncomfortable sound pressure evaluation system 200 according to illustrative Embodiment 2.

FIG. 15 shows a functional block construction of an uncomfortable sound pressure evaluation system 200 according to the present embodiment.

The uncomfortable sound pressure evaluation system 200 includes a sound stimulation output section 10, a measurement section 50, an HTL input section 90, and an uncomfortable sound pressure evaluation apparatus 2. Blocks which are identical to those in FIG. 9 will be denoted by like numerals, and their description will be omitted. Note that the hardware construction of the uncomfortable sound pressure evaluation apparatus 2 is as shown in FIG. 11. As a program which defines different processes from the program 35 (FIG. 11) is executed, the uncomfortable sound pressure evaluation apparatus 2 of the present embodiment as shown in FIG. 15 is realized.

The uncomfortable sound pressure evaluation apparatus 2 of the present embodiment differs from the uncomfortable sound pressure evaluation apparatus 1 of Embodiment 1 in that an uncomfortable sound pressure estimation section 67, an estimation result correction section 69, and a sound stimulation determination section 71 are provided instead of the estimation section 60, the correction section 66, and the sound stimulation determination section 70, and that an estimation result convergence determination section 68 is newly introduced. The details of each component element and the operation of the uncomfortable sound pressure evaluation apparatus 2 will be specifically described later. Hereinafter, the uncomfortable sound pressure estimation section 67 may be referred to as an "estimation section 67", the estimation result correction section 69 a "correction section 69", and the estimation result convergence determination section 68 a "convergence determination section 68".

The uncomfortable sound pressure evaluation apparatus 2 may at least include the extraction section 55, the estimation section 67, the maximum uncomfortable sound pressure determination section 65, the convergence determination section 68, and the correction section 69. In the present specification, these may be referred to as an "uncomfortable sound pressure adjustment apparatus 111", which is implemented as a semiconductor chip circuit. Instead of a semiconductor chip circuit, it may be implemented as a CPU which is provided within a PC, where, by executing a computer program, the CPU is able to realize the function of each component element described later.

Hereinafter, the estimation section 67, the convergence determination section 68, the correction section 69, and the sound stimulation determination section 71 will be described.

<Uncomfortable Sound Pressure Estimation Section 67 (Estimation Section 67)>

Similarly to the estimation section 60 according to Embodiment 1, the estimation section 67 determines an uncomfortable sound pressure (estimated UCL) of the user 5 by referring to characteristic amounts for the first sound, second sound, and third sound which are extracted by the extraction section 55 and a predetermined criterion which previously defines associations between characteristic amounts and uncomfortable sound pressure values. The difference between the estimation section 67 and the estimation section 60 is the timing with which an estimated UCL is determined. The estimation section 60 according to Embodiment 1 determines an uncomfortable sound pressure when the number of summations of event-related potential becomes equal to or greater than a predetermined value. On the other hand, the estimation section 67 according to the present embodiment estimates a UCL for each of the right or left ear and for each frequency each time a sound stimulation group for each of the right or left ear and for each frequency is presented, and an event-related potential is added. This means that an estimated UCL is generated each time a sound stimulation group is presented. The estimated UCL is sent to the convergence determination section 68.

The estimated UCL which is sent each time an event-related potential is added does not need to have been estimated by using an arithmetic mean characteristic amount which is obtained by taking an arithmetic mean of all of the characteristic amounts for each of the right or left ear and for each frequency that have hitherto been received from the extraction section 55. The electroencephalogram of the user 5 which is measured by the measurement section 50 will change under the influence of fluctuations in impedance between the electrodes and the scalp, changes in the user's arousal level and psychological state during measurement, and taming with respect to sound stimulations, for example. Therefore, the following constraints are preferably used in selecting characteristic amounts for arithmetic mean. For each of the right or left ear and for each frequency, the characteristic amounts hitherto received from the extraction section 55 in chronological order are divided into n blocks; one characteristic amount is randomly selected for each block; and an arithmetic mean of these is taken. Using a characteristic amount which is arithmetic-meaned by such a method makes it possible to realize a UCL estimation which is not susceptible to the aforementioned fluctuations in the electroencephalogram of the user 5.

<Estimation Result Convergence Determination Section 68 (Convergence Determination Section 68)>

By using the estimated UCL for each of the right or left ear and for each frequency that is received from the estimation section 67 each time an event-related potential is added, the convergence determination section 68 determines whether the estimated UCLs consecutively obtained for each of the right or left ear and for each frequency have converged or not. The convergence determination section 68 stores an estimated UCL for each of the right or left ear and for each frequency, and for each number of summations of event-related potential; and from their change pattern, the convergence determination section 68 determines whether the estimated UCL have converged or not.

FIG. 16 shows examples of estimated UCLs stored in the convergence determination section 68. Since the number of summations for event-related potentials differs for each of the right or left ear and for each frequency, a different number of estimated UCLs is recorded for each of the right or left ear and for each frequency. Moreover, the convergence determination section 68 stores information as to whether the estimated UCLs have converged or not.

FIG. 17 shows example results of convergence determination stored in the convergence determination section 68. In FIG. 17, the stored results of convergence determination reads "1" when convergence has occurred, and "0" when converge has not occurred. Convergence determination for estimated UCLs may be made in the following manners, for each of the right or left ear and for each frequency: convergence is recognized when the same estimated UCL has repeated three times; or convergence is recognized when the absolute value of a difference between estimated UCLs from an immediately-previous, predetermined number of times is equal to or less than 5 dB, for example. The convergence determination section 68 sends the final estimated UCL and the result of convergence determination for each of the right or left ear and for each frequency to the correction section 69.

Moreover, for example, users lacking stable contact between the electrodes and the scalp and users who frequently blink or make body movements will have a lot of noise broadly mixed during the electroencephalogram measurement, and it is predictable that their estimated UCLs are unstable irrespective of frequency. In the case where the estimated UCLs do not converge irrespective of frequency, the convergence determination section 68 may notify tester or user that the electroencephalogram is not being correctly measured.

Note that, in the electroencephalogram of one participant who was excluded from analysis in the inventors' experiment, noise was mixed in almost the entire length of measurement.

<Estimation Result Correction Section 69 (Correction Section 69)>

Similarly to the correction section 66 according to Embodiment 1, the correction section 69 compares the estimated UCL for each of the right or left ear and for each frequency against the maximum uncomfortable sound pressure to determine whether the estimated UCL is the higher. Then, if the estimated UCL is higher than the maximum uncomfortable sound pressure, the estimated UCL is corrected to the maximum uncomfortable sound pressure. This correct UCL is referred to as the "corrected UCL". The correction section 69 differs from the correction section 66 in terms of timing of correction, and in the fact that a result of convergence determination is sent to the sound stimulation determination section 71. Correction is made at the timing when a result of convergence determination for each of the right or left ear and for each frequency received from the convergence determination section 68 is determined as indicating convergence. If the result of convergence determination indicates no convergence, correction is not performed. It may be each time an event-related potential is added, or only at the timing when the result of convergence determination changes, that the result of convergence determination is sent to the sound stimulation determination section 71.

<Sound Stimulation Determination Section 71>

Similarly to the sound stimulation determination section 70, the sound stimulation determination section 71 determines information of the plural sound stimulations to be presented to the user 5. The sound stimulation determination section 71 differs from the sound stimulation determination section according to Embodiment 1 in that, if convergence is recognized based on the result of convergence determination for each of the right or left ear and for each frequency received from the correction section 69, a sound stimulation group is determined so that this sound stimulation will not be presented. However, when there are only two kinds of sound stimulation groups left, the kinds of sound stimulation groups will be made no fewer. This can reduce the influence of electroencephalogram taming, which may occur as sound stimulations of the same frequency are repeatedly presented.

<Processing by the Uncomfortable Sound Pressure Evaluation System 200>

Figure 18:
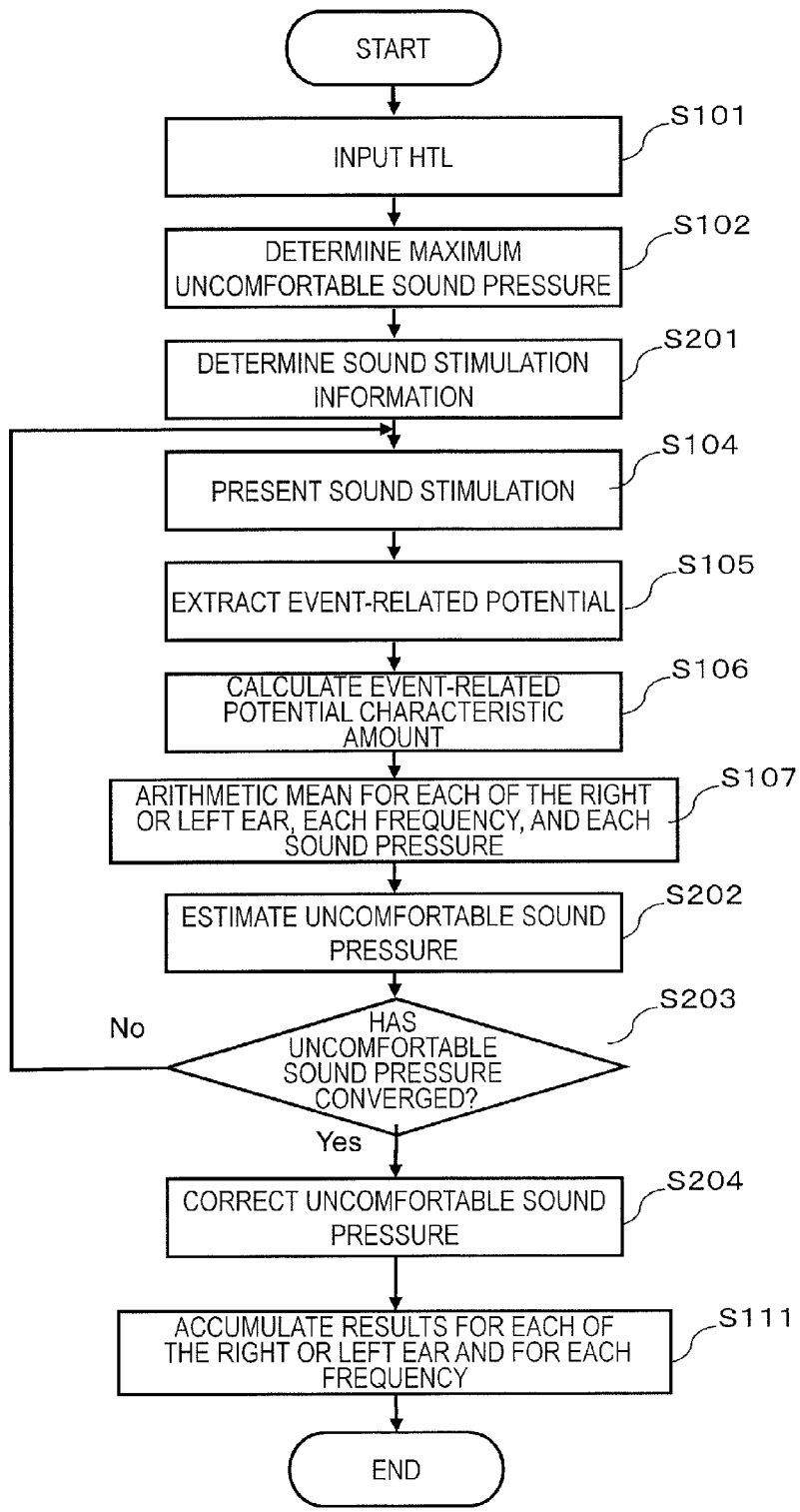
FIG. 18 is a flowchart showing a procedure of processing performed in the uncomfortable sound pressure evaluation system 200.

Next, with reference to FIG. 18, a procedure of processing performed by the uncomfortable sound pressure evaluation system 200 of FIG. 15 will be described. FIG. 18 is a flowchart showing a procedure of processing performed in the uncomfortable sound pressure evaluation system 200. Steps of conducting identical processes to those of the uncomfortable sound pressure evaluation system 100 shown in FIG. 14 will be denoted by like reference numerals, and their description will be omitted.

The processing by the uncomfortable sound pressure evaluation system 200 according to the present embodiment differs from the uncomfortable sound pressure evaluation system 100 of Embodiment 1 in that steps S201 to S204 related to convergence determination for estimated UCLs are added.

At step S201, the sound stimulation determination section 71 determines sound stimulation group information. In addition to determining the frequency, interval of presenting the sound stimulation group, and the like similarly to step S103, step S201 relies on the result of convergence determination for the estimated UCL to determine that the corresponding sound stimulation group is not to be presented when convergence is recognized. However, the number of kinds of sound stimulation groups may no longer be decreased when there are only two kinds of sound stimulation groups. This can reduce the influence of electroencephalogram taming, which may occur as sound stimulations of the same frequency are repeatedly presented.

At step S202, each time the extraction section 55 takes an arithmetic mean of event-related potential, the estimation section 67 estimates a UCL.

At step S203, the estimation result convergence determination section 68 makes a convergence determination for estimated UCLs for each of the right or left ear and for each frequency. Then, the estimated UCL and the result of convergence determination are sent to the correction section 69.

At step S204, the correction section 69 compares the estimated UCL for each of the right or left ear and for each frequency against the maximum uncomfortable sound pressure to determine whether the estimated UCL is the higher. Then, if the estimated UCL is higher than the maximum uncomfortable sound pressure, a corrected UCL is obtained by correcting the estimated UCL to the maximum uncomfortable sound pressure, and a result of convergence determination is sent to the sound stimulation determination section 71. UCL correction may be made at the timing when a result of convergence determination for each of the right or left ear and for each frequency received from the convergence determination section 68 is determined as indicating converge anew. If the result of convergence determination indicates no convergence, correction is not performed. It may be each time an event-related potential is added, or only at the timing when the result of convergence determination changes, that the result of convergence determination is sent to the sound stimulation determination section 71.

With the uncomfortable sound pressure evaluation system 200 of the present embodiment, a UCL estimation is realized in a short time by using an electroencephalogram in response to a sound stimulation as an index, and this estimated UCL can be adjusted into an appropriate range. This realizes a safe hearing aid fitting which does not hurt the user's ear by presenting an overbearing sound when adjusting the hearing aid with an estimated UCL.

The convergence determination section 65 makes convergence determination for estimated UCLs in such a manner that convergence is recognized when the same estimated UCL has repeated three times for each of the right or left ear and for each frequency, for example. The fact that the estimated UCL according to the present technique is based on average values implies that the degree of change in the average value will reduce with increased numbers of summations. Therefore, when a summation value taken over a predetermined number of times results in a value of estimated UCL which far exceeds the upper limit value, it is often the case that the upper limit value will remain exceeded no matter if the number of summations is further increased.

For example, in the case where the upper limit value for UCL at a given frequency is 90 dB but the estimated UCL value continues to be 100 dB, additional summations may not help it reduce to 90 dB or less. Therefore, in such a case, it may be determined that test sounds need to be heard no further, irrespective of the convergence criterion employed at the convergence determination section 65.

An uncomfortable sound pressure evaluation system according to an embodiment of the present invention is useful for the adjustment of a hearing aid at a hearing aid shop, a household, etc., because a UCL which has been estimated as indexed by an electroencephalogram in response to a sound stimulation can be adjusted into an appropriate range based on a distribution of actually-measured UCLs acquired from the user. Also for a person with normal hearing, by estimating his or her uncomfortable sound pressure in advance, applications will become possible such as setting a maximum sound volume for an audio device of a television set or a stereo set.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortable sound pressure evaluation system comprising:
   a measurement section configured to measure an electroencephalogram signal of a user;
   an output section configured to consecutively present a plurality of sound stimulation groups to the user, each sound stimulation group including at least one sound stimulation, and the sound stimulation groups differing in frequency from one another;
   an extraction section configured to extract, for each sound stimulation group, information concerning event-related potential from the electroencephalogram signal in a predetermined zone defined based on a point of presenting the at least one sound stimulation as a starting point;
   an estimation section configured to estimate an uncomfortable sound pressure of the user from the information concerning event-related potential against a predefined criterion;
   a storage section configured to store a predefined maximum uncomfortable sound pressure; and
   a correction section configured to determine whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

2. An uncomfortable sound pressure evaluation system comprising:

a measurement section configured to measure an electroencephalogram signal of a user;

an output section configured to present a sound stimulation group to the user, the sound stimulation group including a first sound, a second sound, and a third sound which are pure tones of a same frequency and which consecutively decrease in sound pressure within a predetermined range;

an extraction section configured to extract a characteristic amount concerning time frequency information of event-related potential from the electroencephalogram signal in a predetermined zone defined based on a point of presenting each of the first sound, the second sound, and the third sound as a starting point;

an estimation section configured to estimate, based on the extracted characteristic amount, an uncomfortable sound pressure corresponding to the frequency;

a maximum uncomfortable sound pressure determination section configured to determine, based on a hearing threshold value of the user, a maximum uncomfortable sound pressure of the user corresponding to the frequency; and a correction section configured to correct the uncomfortable sound pressure to the maximum uncomfortable sound pressure and to output the corrected uncomfortable sound pressure if the estimated uncomfortable sound pressure is higher than the maximum uncomfortable sound pressure, and to output the estimated uncomfortable sound pressure if the estimated uncomfortable sound pressure is equal to or lower than the maximum uncomfortable sound pressure.

3. The uncomfortable sound pressure evaluation system of claim 2, wherein the maximum uncomfortable sound pressure determination section retains in advance a predetermined table concerning maximum uncomfortable sound pressures associated with hearing threshold values, and determines the maximum uncomfortable sound pressure from a given hearing threshold value of the user by referring to the table.

4. The uncomfortable sound pressure evaluation system of claim 3, wherein, for each of a plurality of frequencies, the output section outputs a sound stimulation group including a first sound, a second sound, and a third sound;

the extraction section extracts a characteristic amount concerning time frequency information of event-related potential for each sound stimulation group;

the estimation section estimates an uncomfortable sound pressure corresponding to each frequency, based on the characteristic amount extracted for each sound stimulation group; and for the respective estimated uncomfortable sound pressure corresponding to each frequency, the correction section corrects the uncomfortable sound pressure to the maximum uncomfortable sound pressure and outputs the corrected uncomfortable sound pressure if the uncomfortable sound pressure is higher than the maximum uncomfortable sound pressure, and outputs the estimated uncomfortable sound pressure if the estimated uncomfortable sound pressure is equal to or lower than the maximum uncomfortable sound pressure.

5. The uncomfortable sound pressure evaluation system of claim 3, wherein, for each of a plurality of frequencies, the output section outputs a sound stimulation group including a first sound, a second sound, and a third sound;

the extraction section extracts a characteristic amount concerning time frequency information of event-related potential for each sound stimulation group;

the estimation section estimates an uncomfortable sound pressure corresponding to each frequency, based on the characteristic amount extracted for each sound stimulation group; and for the respective estimated uncomfortable sound pressure corresponding to each frequency, the correction section determines whether the uncomfortable sound pressure is higher than the maximum uncomfortable sound pressure or not, and if, among determination results, a proportion of those determination results which indicate the uncomfortable sound pressure to be higher than the maximum uncomfortable sound pressure is equal to or greater than predetermined, outputs the estimated uncomfortable sound pressure for all frequencies.

6. The uncomfortable sound pressure evaluation system of claim 5, wherein, among the determination results, if a proportion of those determination results which indicate the uncomfortable sound pressure to be higher than the maximum uncomfortable sound pressure is smaller than predetermined, the correction section corrects the uncomfortable sound pressure to the maximum uncomfortable sound pressure and outputs the corrected uncomfortable sound pressure, for each uncomfortable sound pressure determined to be higher than the maximum uncomfortable sound pressure.

7. The uncomfortable sound pressure evaluation system of claim 2, further comprising a database for accumulating the uncomfortable sound pressure that is output from the correction section for the frequency.

8. The uncomfortable sound pressure evaluation system of claim 7, wherein, the correction section generates correction information indicating whether the estimated uncomfortable sound pressure is corrected or not; and the database accumulates the correction information in association with the uncomfortable sound pressure for the frequency.

9. The uncomfortable sound pressure evaluation system of claim 2, wherein, the output section presents a sound stimulation group of the same frequency and sound pressures as those of the first sound, the second sound, and the third sound a plurality of times at a predetermined interval;

each time the sound stimulation group is presented, the extraction section extracts an event-related potential from the electroencephalogram signal in a predetermined zone defined based on a point of presenting each of the first sound, the second sound, and the third sound of each sound stimulation group as a starting point, and adds the event-related potential to the already extracted event-related potential or event-related potentials; and each time the sound stimulation group is presented, the estimation section estimates an uncomfortable sound pressure based on the added event-related potential.

10. The uncomfortable sound pressure evaluation system of claim 9, further comprising a convergence determination section configured to determine, each time the sound stimulation group is presented, whether the estimated uncomfortable sound pressure has converged or not, wherein, for any sound stimulation group being determined by the convergence determination section as having reached convergence, the output section stops subsequent presentation.

11. The uncomfortable sound pressure evaluation system of claim 2, wherein the extraction section extracts a wavelet-coefficient related characteristic amount concerning the event-related potential.

12. The uncomfortable sound pressure evaluation system of claim 11, wherein the estimation section retains as training data a previously-provided relationship between wavelet characteristic amounts and sound pressures of other people, and performs linear discrimination by using the characteristic amount extracted by the extraction section and the training data to estimate the uncomfortable sound pressure.

13. The uncomfortable sound pressure evaluation system of claim 11, wherein, based on an event-related potential of the electroencephalogram signal extraction section measured in a time zone of 300 ms or less defined from a point of presenting each of the first sound, the second sound, and the third sound as a starting point, and extracts a wavelet coefficient of the event-related potential as the characteristic amount.

14. The uncomfortable sound pressure evaluation system of claim 10, wherein the extraction section extracts as the characteristic amount a value obtained by averaging wavelet coefficients of the event-related potential over a predetermined frequency range and a predetermined time range.

15. The uncomfortable sound pressure evaluation system of claim 14, wherein the predetermined frequency range is between 5 Hz and 15 Hz.

16. The uncomfortable sound pressure evaluation system of claim 14, wherein the predetermined time range is 50 ms.

17. An uncomfortable sound pressure adjustment apparatus for use in an uncomfortable sound pressure evaluation system,
the uncomfortable sound pressure evaluation system including an output section configured to consecutively present a plurality of sound stimulation groups to a user, each sound stimulation group including at least one sound stimulation, and the sound stimulation groups differing in frequency from one another, the uncomfortable sound pressure adjustment apparatus comprising:
an extraction section configured to receive from a measurement section which measures an electroencephalogram signal of the user the electroencephalogram signal, and for each sound stimulation group, to extract information concerning event-related potential from the electroencephalogram signal in a predetermined zone defined based on a point of presenting the at least one sound stimulation as a starting point;
an estimation section configured to estimate an uncomfortable sound pressure of the user from the information concerning event-related potential against a predefined criterion;
a storage section configured to store a predefined maximum uncomfortable sound pressure; and
a correction section configured to determine whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

18. An uncomfortable sound pressure evaluation apparatus comprising:
the uncomfortable sound pressure adjustment apparatus of claim 17;
a sound stimulation determination section configured to determine the at least one sound stimulation; and
a sound stimulation generation section configured to generate the determined at least one sound stimulation, and to output to the extraction section information of a point of outputting the at least one sound stimulation.

19. An uncomfortable sound pressure evaluation method comprising the steps of:
receiving from a measurement section which measures an electroencephalogram signal of a user the electroencephalogram signal;
consecutively presenting a plurality of sound stimulation groups to the user, each sound stimulation group including at least one sound stimulation, and the sound stimulation groups differing in frequency from one another;
for each sound stimulation group, extracting information concerning event-related potential from the electroencephalogram signal in a predetermined zone defined based on a point of presenting the at least one sound stimulation as a starting point;
estimating an uncomfortable sound pressure of the user from the information concerning event-related potential against a predefined criterion; and
determining whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

20. A non-transitory computer-readable medium having thereon a computer program to be executed by a computer mounted in an uncomfortable sound pressure evaluation apparatus,
wherein the computer program causes the computer to execute the steps of:
receiving from a measurement section which measures an electroencephalogram signal of a user the electroencephalogram signal;
consecutively presenting a plurality of sound stimulation groups to the user, each sound stimulation group including at least one sound stimulation, and the sound stimulation groups differing in frequency from one another;
for each sound stimulation group, extracting information concerning event-related potential from the electroencephalogram signal in a predetermined zone defined based on a point of presenting the at least one sound stimulation as a starting point;
estimating an uncomfortable sound pressure of the user from the information concerning event-related potential against a predefined criterion; and
determining whether the estimated uncomfortable sound pressure is higher than the maximum uncomfortable sound pressure or not, and if, among determination results across all of the plurality of sound stimulation groups, a proportion of those determination results which indicate the uncomfortable sound pressure to be higher than the maximum uncomfortable sound pressure is smaller than predetermined, correcting each uncomfortable sound pressure determined as higher than the maximum uncomfortable sound pressure to a sound pressure equal to or less than the maximum uncomfortable sound pressure.

\* \* \* \* \*